US009028858B2

(12) United States Patent
Nielsen et al.

(10) Patent No.: US 9,028,858 B2
(45) Date of Patent: May 12, 2015

(54) ASSEMBLY FOR THE PREPARATION OF A MEDICAL DEVICE HAVING A COATING COMPRISING HYDROGEN PEROXIDE

(75) Inventors: Bo Rud Nielsen, Allerod (DK); Soren Kristiansen, Hundested (DK); Bo Kjellman Bruun, Copenhagen O (DK); Martin Sidenius, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 437 days.

(21) Appl. No.: 10/547,147

(22) PCT Filed: Feb. 26, 2004

(86) PCT No.: PCT/DK2004/000129
§ 371 (c)(1),
(2), (4) Date: Jun. 27, 2006

(87) PCT Pub. No.: WO2004/075944
PCT Pub. Date: Sep. 10, 2004

(65) Prior Publication Data
US 2006/0263404 A1 Nov. 23, 2006

(30) Foreign Application Priority Data

Feb. 26, 2003 (DK) ................................ 2003 00296
Feb. 26, 2003 (DK) ................................ 2003 00298

(51) Int. Cl.
| | |
|---|---|
| A61F 2/00 | (2006.01) |
| B65D 83/10 | (2006.01) |
| B65D 30/22 | (2006.01) |
| A61M 25/00 | (2006.01) |
| A61L 29/08 | (2006.01) |
| A61L 29/16 | (2006.01) |

(52) U.S. Cl.
CPC .......... *A61M 25/0017* (2013.01); *A61L 29/085* (2013.01); *A61L 29/16* (2013.01); *A61L 2300/404* (2013.01); *A61M 25/002* (2013.01); *A61M 2025/0056* (2013.01)

(58) Field of Classification Search
USPC ............ 424/422; 604/265; 427/2.1; 206/571, 206/364
See application file for complete search history.

(56) References Cited

U.S. PATENT DOCUMENTS

| | | | |
|---|---|---|---|
| 3,307,910 A | 3/1967 | Ryckaert | |
| 3,967,728 A | 7/1976 | Gordon et al. | |
| 4,119,094 A | 10/1978 | Micklus et al. | |
| 4,373,009 A | 2/1983 | Winn | |
| 4,437,567 A * | 3/1984 | Jeng ............................... | 206/210 |
| 4,459,317 A | 7/1984 | Lambert | |
| 4,477,438 A | 10/1984 | Willcockson | |
| 4,515,593 A | 5/1985 | Norton | |
| 4,754,877 A | 7/1988 | Johansson et al. | |
| 4,792,914 A | 12/1988 | Dartois et al. | |
| 4,863,445 A | 9/1989 | Mayhan et al. | |
| 4,889,689 A * | 12/1989 | Tsao ............................... | 422/30 |
| 4,895,566 A | 1/1990 | Lee | |
| 4,917,686 A | 4/1990 | Bayston et al. | |
| 5,008,106 A | 4/1991 | Merianos et al. | |
| 5,041,100 A | 8/1991 | Rowland et al. | |
| 5,049,140 A | 9/1991 | Brenner et al. | |
| 5,120,816 A | 6/1992 | Gould et al. | |
| 5,130,124 A | 7/1992 | Merianos et al. | |
| 5,296,583 A * | 3/1994 | Levy ............................... | 528/72 |
| 5,312,319 A | 5/1994 | Salter | |
| 5,312,619 A | 5/1994 | Shih et al. | |
| 5,357,636 A | 10/1994 | Dresdner, Jr. et al. | |
| 5,589,507 A * | 12/1996 | Hall et al. ...................... | 514/557 |
| 5,882,526 A | 3/1999 | Brown et al. | |
| 5,951,458 A | 9/1999 | Hastings et al. | |
| 6,059,107 A | 5/2000 | Nøsted et al. | |
| 6,203,536 B1 | 3/2001 | Berg et al. | |
| 6,617,291 B1 * | 9/2003 | Smith ........................... | 510/112 |
| 6,986,868 B2 | 1/2006 | Madsen | |

(Continued)

FOREIGN PATENT DOCUMENTS

| | | |
|---|---|---|
| CN | 1031650 A | 3/1989 |
| CN | 101171040 | 4/2008 |

(Continued)

OTHER PUBLICATIONS

Niels Linnet: "pH measurements in theory and practice", 1.ed., Radiometer A/S, Copenhagen, 1970.
Encyclopedia of Polymer Science and Engineering, eds. H.F. Mark; N. M. Bikales, C.G. Overberger, and G. Menges, 2. ed., vol. 13, pp. 292-294, Wiley-Interscience, New York, 1988.
De Kimpe, Sjef J., et al. "Reactive Oxygen Species Regulate Macrophage Scavenger Receptor Type I, but Not Type II, in the Human Monocytic Cell Line THP-1" Molecular Pharmacology, vol. 53, 1998, p. 1076-1082.

(Continued)

*Primary Examiner* — Juliet Switzer
*Assistant Examiner* — Caralynne Helm
(74) *Attorney, Agent, or Firm* — Coloplast Corp., Coloplast A/S; Nick Baumann

(57) ABSTRACT

The present invention provides an assembly for the preparation of a medical device having a porous coating comprising hydrogen peroxide. Particularly interesting medical devices are catheters (such as urinary catheters), endoscopes, laryngoscopes, tubes for feeding, tubes for drainage, guide wires, condoms, urisheaths, barrier coatings e.g. for gloves, stents and other implants, extra corporeal blood conduits, membranes e.g. for dialysis, blood filters, devices for circulatory assistance, dressings for wound care, and ostomy bags. The coating is in particular a hydrophilic coating formed from cross-linked polyvinylpyrrolidone. In one embodiment, the assembly holds a dry catheter element in one compartment of a package and an aqueous hydrogen peroxide solution in another compartment. The solution may also comprise stabilizers, e.g. chelators, and osmolality increasing agents. The catheter for insertion in the urethra is useful for the treatment, alleviation or prophylaxis of microbial infections such as urinary tract infections (UTI).

7 Claims, 2 Drawing Sheets

(56) References Cited

U.S. PATENT DOCUMENTS

| | | | |
|---|---|---|---|
| 7,833,475 B2 | 11/2010 | Madsen | |
| 8,487,284 B2 | 7/2013 | Tateshima et al. | |
| 2001/0001443 A1* | 5/2001 | Kayerod et al. | 206/364 |
| 2002/0031601 A1 | 3/2002 | Darouiche et al. | |
| 2002/0037943 A1* | 3/2002 | Madsen | 522/86 |
| 2002/0120333 A1 | 8/2002 | Keogh et al. | |
| 2002/0156440 A1 | 10/2002 | Israelsson et al. | |
| 2002/0192297 A1* | 12/2002 | Ramirez et al. | 424/605 |
| 2003/0065292 A1* | 4/2003 | Darouiche et al. | 604/265 |
| 2004/0074794 A1* | 4/2004 | Conway et al. | 206/364 |
| 2005/0214443 A1 | 9/2005 | Madsen | |
| 2011/0106061 A1 | 5/2011 | Madsen et al. | |

FOREIGN PATENT DOCUMENTS

| | | |
|---|---|---|
| DE | 41 42 319 A1 | 6/1993 |
| DK | 170883 | 10/1983 |
| EP | 0 093 093 | 11/1983 |
| EP | 0 217 771 A1 * | 4/1987 |
| EP | 0265381 | 4/1988 |
| EP | 0306212 | 8/1988 |
| EP | 0 379 156 | 7/1990 |
| EP | 0 389 632 | 10/1990 |
| EP | 0 454 293 | 10/1991 |
| EP | 0 923 398 B1 | 6/1999 |
| EP | 0 935 478 | 8/1999 |
| EP | 1 131 112 | 9/2001 |
| EP | 1 252 898 | 10/2002 |
| GB | 409361 | 10/1932 |
| GB | 1500707 | 2/1978 |
| GB | 1 600 963 | 10/1981 |
| JP | 55-12265 | 3/1980 |
| JP | 58-118765 | 7/1983 |
| JP | 2001-500414 | 1/2001 |
| JP | 2001-511659 | 8/2001 |
| WO | WO 86/06284 | 11/1986 |
| WO | WO 89/04674 | 6/1989 |
| WO | WO 90/05162 | 5/1990 |
| WO | WO 91/09807 | 7/1991 |
| WO | WO 9109807 A2 * | 7/1991 |
| WO | WO 91/19756 | 12/1991 |
| WO | WO 94/16747 | 8/1994 |
| WO | WO 97/42901 | 11/1997 |
| WO | WO 98/11932 | 3/1998 |
| WO | WO 98/19729 | 5/1998 |
| WO | WO 98/31420 * | 7/1998 |
| WO | WO 98/58990 * | 12/1998 |
| WO | WO 99/03523 | 1/1999 |
| WO | WO 99/65538 | 12/1999 |
| WO | WO 00/30696 | 6/2000 |
| WO | WO 00/47494 * | 8/2000 |
| WO | WO 01/43807 | 6/2001 |
| WO | WO 02/26277 | 4/2002 |
| WO | WO 02/26277 A2 | 4/2002 |
| WO | WO 02/100455 A2 | 12/2002 |
| WO | WO 03/092779 A1 | 11/2003 |
| WO | WO 2006/117372 | 11/2006 |

OTHER PUBLICATIONS

Kuczynski, Krzysztof, et al. "DTPMPA: polyamino polyphosphonic acid and its use in paper processes" Tappi Journal, vol. 71(6), 1998, pp. 171-174.

Xu, E.C., "H2O2 Bleaching of Mechanical Pulps, Part IV: H2O2 Consumption" Journal of pulp and paper science vol. 28(11), 2002, pp. 379-383.

Jaschinski, T. et al., "Use of high temperature resistant chelants in peroxide bleaching of kraft pulps" Pulp and Paper Canada, vol. 99(8), 1998, pp. 52-56.

Kassem, Aly A. et al. "Further investigation on the effect of iron as a catalyst on the stability of hydrogen peroxide solution and its action in presence of different stabilizers." Bulletin of Faculty of Pharmacy, Cairo University, vol. 10(1), 1971, pp. 265-273.

* cited by examiner

ASSEMBLY FOR THE PREPARATION OF A MEDICAL DEVICE HAVING A COATING COMPRISING HYDROGEN PEROXIDE

This is a nationalization of PCT/DK04/000129 filed Feb. 26, 2004 and published in English.

FIELD OF THE INVENTION

The present invention relates to an assembly which is useful for providing a medical device having on at least a part of the surface thereof a coating of a porous polymer composition, e.g. a hydrophilic coating, wherein said coating comprises a liquid, e.g. a liquid swelling medium, which comprises hydrogen peroxide.

The present invention also relates to a medical device as such, a particular swelling medium containing hydrogen peroxide, and the medical use of the assembly and the medical device.

BACKGROUND OF THE INVENTION

In many medical applications, a polymer composition constituting at least a part of a medical device, such as a hydrophilic coating, a hydrogel, a scaffold, an adhesive, etc., is intended to be in intimate contact with the human body. Medical devices may be intended for introduction into, covering, or filling human cavities. Examples of cavities, or openings, may be naturally occurring cavities such as urethra, mouth, ear, nose, eye, rectum, or it could be man-made openings made by surgery or as a result of a planned action, e.g. a cavity or an opening in an artery, a vein, a lymph node, or an opening in the gastrointestinal tract, such as a colostomy, ileostomy, urostomy or an opening or cavity resulting from a non-anticipated action. Said medical device or the polymer composition may also be used for location between extremities (legs, fingers, toes, armpit) or for physical attachment to the human body as a result of the involvement of an adhesive.

Polymer compositions of medical devices can be engineered to be soft and flexible, and to reduce friction between sliding parts. For example, it is known to coat medical devices, e.g. catheters for introduction into human cavities such as blood vessels, digestive organs and the urinary system, with a hydrophilic coating. When the coating is swelled with an aqueous solution or water, the surface of the medical device becomes slippery and is well suited for a painless introduction into a cavity with minimum damage on tissue.

Where a device of said type, e.g. a catheter with a hydrophilic coating, is introduced into a human cavity, the normal human defense barrier may be penetrated resulting in introduction of microbes, i.e. small cells such as vira, bacteria, fungi, mold, bacteriophages, or tissue-like or multiple organized cells. It is well known that persons practicing intermittent urethral catheterization as a daily routine often have problems with symptomatic urinary tract infections (UTI). Similarly, a number of other medical devices that come in intimate contact with human tissue can cause microbial infections.

Hydrogen peroxide is known to have an anti-microbial effect. It is also known to decompose easily. By reaction with reduced transition metal ions such as iron (II) and copper (I), hydrogen peroxide decomposes by the Fenton reaction to form the highly reactive hydroxyl radical. Apart from destroying hydrogen peroxide and hence reducing the shelf-life of a product comprising hydrogen peroxide, hydroxyl radicals from the Fenton reaction may potentially damage a polymer coating, in particular a hydrophilic coating, by way of its reaction with various components of the coating system. Contamination of water with transition metal ions takes place, e.g. by storage of the water in steel tanks or in glass. Even in water that is purified, e.g. by ion exchange, trace amounts of transitional metal ions are still present. Thus, a polymer coating comprising a liquid comprising hydrogen peroxide may generally be considered unsuited for long time storage.

U.S. Pat. No. 5,130,124 discloses a stabilized film-forming antimicrobial composition of hydrogen peroxide.

U.S. Pat. No. 5,951,458 discloses a method of inhibiting restenosis by application of an oxidizing agent to blood vessels, e.g. by delivery of hydrogen peroxide via a balloon catheter. The US-patent does not address the problem of stability of hydrogen peroxide when present in a hydrophilic coating.

SUMMARY OF THE INVENTION

The present invention utilizes the beneficial properties of hydrogen peroxide ($H_2O_2$) while at the same time including means to avoid the potentially detrimental effects arising from the unstability of hydrogen peroxide.

A first aspect of the present invention relates to an assembly comprising (i) at least one medical device element having a coating of a porous polymer composition, said coating covering at least a part of said element(s), (ii) at least one liquid for occupying the pores of said polymer composition, (iii) a hydrogen peroxide source, and (iv) packing means, said packing means being adapted to hold said medical device element(s), said liquid(s) and said hydrogen peroxide source in at least two separate compartments.

A second aspect of the present invention relates to an antimicrobial liquid swelling medium consisting of:
0.1-3.0% (w/w) of hydrogen peroxide,
25-1200 mg/L of one or more stabilizers,
0-10 mM of one or more buffers,
0-300 mM osmolality increasing agents,
0-2000 mg/L of other constituents, and
the balance of pure water,
and has a pH in the range of 2.0-8.5.

A third aspect of the present invention relates to a medical device having on at least a part of the surface thereof a coating of a porous polymer composition, wherein said coating comprises a liquid that comprises hydrogen peroxide and an agent that stabilizes hydrogen peroxide.

A fourth aspect of the present invention relates to a method of treatment, alleviation or prophylaxis of microbial infections wherein a medical device, in a first step, is prepared from the assembly defined above, and, in a second step, is brought into contact with a body part of a mammal in need for said medical device.

A fifth aspect of the present invention relates to a method of treatment, alleviation or prophylaxis of microbial infections wherein a medical device, as defined above, is brought into contact with a body part of a mammal in need for said medical device.

A sixth aspect of the present invention relates to an assembly comprising (i) at least one medical device element having a coating of a porous polymer composition, said coating covering at least a part of said element(s), and said coating having present therein a liquid comprising hydrogen peroxide, and (ii) packing means adapted to hold said medical device element(s).

DETAILED DESCRIPTION OF THE INVENTION

The Assembly

Figure 1A:
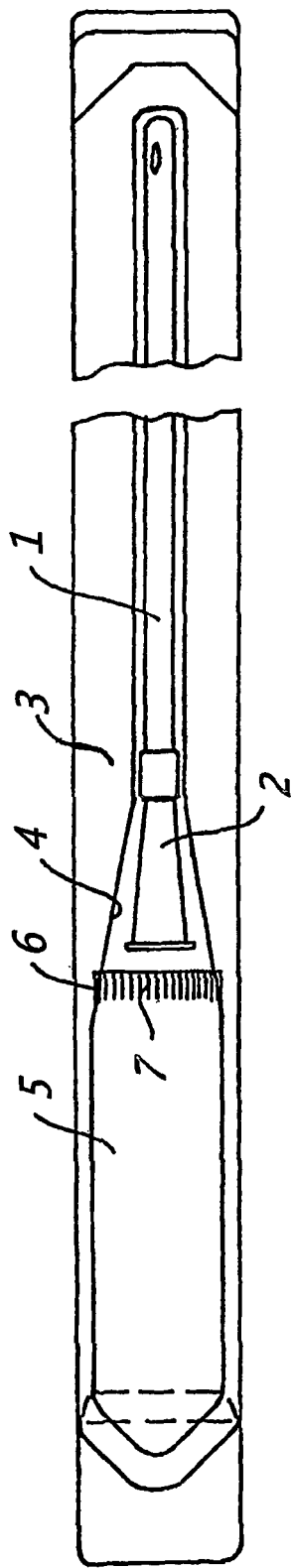
FIGS. 1 and 2 illustrate examples of a packing means with two separate compartments.

In view of the above-mentioned potential problems with respect to stability of hydrogen peroxide, not the least when present in polymer coatings, in particular hydrophilic coatings, the present invention provides an assembly which is useful for the preparation of a medical device immediately before use thereof, where the coating of said device will contain a well-defined amount of hydrogen peroxide.

Thus, the present invention provides a solution to the above-mentioned problems by providing means (i.e. the assembly) for obtaining a medical device having on at least a part of the surface thereof a coating of a porous polymer composition, e.g. a hydrophilic coating, wherein said coating comprises a liquid, e.g. a liquid swelling medium, which comprises hydrogen peroxide.

As it has been shown with the illustrative examples herein, such a medical device efficiently provides advantages with respect to suppression of the development of microbial infections upon use, e.g. urinary tract infections. Furthermore, the above-mentioned stability problems are reduced.

More particularly, the present invention provides an assembly comprising (i) at least one medical device element having a coating of a porous polymer composition, said coating covering at least a part of said element(s), (ii) at least one liquid for occupying the pores of said polymer composition, (iii) a hydrogen peroxide source, and (iv) packing means, said packing means being adapted to hold said medical device element(s), said liquid(s) and said hydrogen peroxide source in at least two separate compartments. In a preferred embodiment thereof, the packing means is further adapted to establish contact between said medical device element(s), said liquid(s), and said hydrogen peroxide source.

Medical Device

The term "medical device" should be interpreted in a fairly broad sense. Suitable examples of medical devices (including instruments) are catheters (such as urinary catheters), endoscopes, laryngoscopes, tubes for feeding, tubes for drainage, guide wires, condoms, urisheaths, barrier coatings e.g. for gloves, stents and other implants, extra corporeal blood conduits, membranes e.g. for dialysis, blood filters, devices for circulatory assistance, dressings for wound care, and ostomy bags. Most relevant are catheters, endoscopes, laryngoscopes, tubes for feeding, tubes for drainage, guide wires, and stents and other implants. Particularly interesting medical devices within the context of the present invention are catheters, such as urinary catheters.

Some medical devices may be constructed of one or more medical device elements which, when being assembled or rearranged, represent the ready-to-use medical device. Reference to a "medical device element" and "catheter element" means the medical device or catheter as such (i.e. one piece medical device or catheter) or a part of a "ready-to-use" medical device or catheter.

Medical devices and medical device elements can be formed from a variety of types of basic materials, such as plastics, metals, glass, ceramics, etc. Typical examples of plastic materials for medical devices are polymers such as polyurethanes and copolymers thereof, or polyether block amides such as Pebax™ or other polymer materials including polyvinyl chloride, polyamide, silicone, styrene-ethylene/butylene-styrene block copolymers (SEBS), styrene-isoprene-styrene block copolymers (SIS), styrene-ethylene/propylene-styrene block copolymers (SEPS), ethylene-vinyl acetate copolymers (EVA), polyethylene (PE), metallocene-catalyzed polyethylene, and copolymers of ethylene and propylene or mixtures of such. Currently very relevant materials are polyurethanes and copolymers thereof.

Within the present context, the medical device has on at least a part of the surface thereof (i.e. on at least a part of the surface of the basic material) a coating of a porous polymer composition, e.g. a hydrophilic coating. In some embodiments, the coating of the porous polymer composition (e.g. the hydrophilic coating) is applied to the full (outer) surface of the substrate polymer, and in some other embodiments, only to a part of the surface. In the most relevant embodiments, the coating is applied to at least a part of the surface (preferably the whole surface) of the medical device that—upon proper use—comes into direct contact with body parts of the person for which the medical device is intended.

In the present context, a polymer composition is "porous" in the sense that (i) the coating of the polymer composition has pore spaces suitable for holding a liquid medium by means of capillary forces, e.g. as exemplified by a sponge, or (ii) the coating of the polymer composition may be porous as a result of hydrophilic properties, e.g. as it is known from swellable hydrophilic polymers that can retain substantive amounts of water within the swelled polymeric network. In some instances, the "porosity" of the polymeric composition may be the result of a combination of the two above-mentioned "phenomena".

Particularly interesting polymer compositions comprise a substantial amount (i.e. at least 50% (w/w)) of swellable hydrophilic polymers forming a hydrophilic coating on at least a part of the surface of the medical device, e.g. a catheter. For some applications, the polymer composition (e.g. hydrophilic polymer such as polyvinylpyrrolidone) may advantageously be cross-linked.

Typical examples of such swellable hydrophilic polymers are polyvinylpyrrolidone, polyvinyl alcohol, poly(meth)acrylic acid, poly(meth)acrylic amides, polyethylene glycol, carboxymethylcellulose, cellulose acetate, cellulose acetate propionate, chitosan, polysaccharides; or any homopolymer or copolymer of two or more of the monomers: N-vinylpyrrolidone, vinyl alcohol, (meth)acrylic acid, (meth)acrylic amides, (meth)acrylic esters such as hydroxyethyl methacrylate, maleic anhydride, maleimide, methyl vinyl ether, alkyl vinyl ethers, and other unsaturated compounds. Furthermore, the hydrophilic polymer may be any blend of these homopolymers or copolymers. Other radiation curing hydrophilic polymers comprising unsaturated vinylic double bonds can also suitably be used for the coating. Such polymers may be made by copolymerising into a prepolymer an acrylic substance like dimethylaminoethylmethacrylate with N-vinyl pyrrolidone, methacrylic acid, methacrylic esters, methyl vinyl ether etc. Such a prepolymer is typically coated to the surface and ultimately radiation cured. The hydrophilic polymer of the coating may further be made by adding monomers of acrylic nature to the above-mentioned types of polymers. Polyethylene glycols and polyvinyl pyrrolidone are particularly useful for such hydrophilic coatings.

Most preferably, the hydrophilic polymer of the coating is selected from the group of polyvinylpyrrolidone or copolymers thereof, e.g. polyvinylpyrrolidone-vinyl acetate copolymers. These types of polymers may furthermore be cross-linked by radiation. When using the pure polyvinylpyrrolidone (poly(N-vinyl-2-pyrrolidone); PVP), various chain lengths may be selected each giving various characteristics to the coating. Typically, such polyvinylpyrrolidone polymers have a number average molecular weight of above 100,000. As an example, PVP K-90 with a molecular weight of 1,200,000 can be selected but other types of PVP with other molecular weights may also be used.

In one interesting embodiment, the substrate polymer is polyurethane and the hydrophilic polymer is polyvinylpyrrolidone.

One or more additives may be included when preparing the hydrophilic coating, e.g. so as to facilitate the cross-linking of the hydrophilic polymer or so as to improve bonding of the polymer to the substrate surface. Such additives are known in the art and may include UV-initiators, e.g. as described in WO 98/58990. An example of a suitable UV-polymerisation initiator is Esacure® KIP 150. Hydrophilic coatings may furthermore comprise plasticizers such as acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, and triethyl phosphate.

A hydrophilic coating may be applied by dipping, spraying or brushing a polymer solution onto the medical device or medical device element, or the part thereof on which the hydrophilic coating is desirable. Alternatively, the coating layer may be formed by co-extrusion.

A polyvinylpyrrolidone coating on a medical device element may be formed by applying a solution containing N-methylpyrrolidone, polyvinylpyrrolidone or copolymers thereof (N-vinylpyrrolidone with poly(meth)acrylic acid, acrylamides, vinyl alcohol, polyethylene glycol, polyvinyl methylether, polyvinyl methyl ether-maleic acid anhydride, carboxymethylcellulose, or hydroxyethylcellulose), optionally using a UV photo-initiator such as Esacure® KIP 150, and a plasticizer dissolved in ethanol.

Before application of the hydrophilic coating, in particular for some of the combinations of substrate polymers and hydrophilic coatings, a primer coating may advantageously be applied before application of the polymer composition that forms the porous polymer composition (e.g. the hydrophilic coating). In some embodiments, the primer coating may be prepared from a dilute solution of the polymer solution.

In the alternative embodiment where the coating of the polymer composition is a "sponge-like" structure having pore spaces suitable for holding a liquid medium by means of capillary forces, the coating may be prepared by co-extruding the basic material of the medical device with a material forming the "sponge-like" structure, or by dipping the basic material of the medical device in a material (or solution thereof) which afterwards—upon curing—expands to the "sponge-like" structure forming the porous coating, etc.

Liquid (Liquid Swelling Medium)

The liquid that is part of the assembly is intended to be contacted with the porous polymer composition upon use in such a manner that the liquid and hydrogen peroxide are allowed to fill the pores of the porous polymer composition. In some embodiments, a part or all of the liquid is initially contained within the porous polymer composition. For hydrophilic polymers (e.g. cross-linked hydrophilic polymers such as cross-linked PVP), the liquid (i.e. a liquid swelling medium) swells the hydrophilic polymer upon contact so as to form a swelled hydrophilic coating.

The assembly may comprise one or more liquids (e.g. liquid swelling medium/media), and if two or more are included, such liquids should preferably be mixable.

In most embodiments, the one or more liquids are selected from water (aqua) and aqueous solutions (e.g. aqueous hydrogen peroxide solutions). Aqueous solutions typically comprise at least 90% (w/w), such as at least 95% (w/w), or at least 97% (w/w), of water.

Hydrogen Peroxide Source

The hydrogen peroxide source is typically selected from liquid hydrogen peroxide sources (i.e. aqueous solutions of hydrogen peroxide) and solid hydrogen peroxide sources (i.e. solid compounds that upon heating or exposure to water release hydrogen peroxide). Liquid hydrogen peroxide sources are preferably stabilized in order to reduce or eliminate decomposition of hydrogen peroxide (see below).

Examples of solid hydrogen peroxide sources are, e.g., hydrogen peroxide bound in chemical compounds (e.g. a solid compound of hydrogen peroxide bound in polyvinylpyrrolidone (PVP)) and compounds with the potential of developing hydrogen peroxide, e.g. by reaction with water, such as perborates (e.g. sodium perborate), percarbonates (e.g. sodium percarbonate), peroxyphosphates (e.g. sodium peroxyphosphate), persulfates (e.g. potassium persulfate), peroxymonosulfates, peroxydisulfates, urea peroxide, etc.

It should be understood that the hydrogen peroxide source referred to herein may consist of one or more of the species of sources, and possibly also a solid source combined with a liquid hydrogen peroxide source.

In order to obtain biocompatibility between the hydrogen peroxide coating composition and the human tissue cells, the concentration of hydrogen peroxide in the liquid (e.g. swelling medium) prior to use should be kept at a low level, such as 0.01-5.0%, such as 0.1-3.0%, such as 0.2-2.0%, such as 1%, as measured (w/w) in the liquid (e.g. swelling medium) of the prepared and ready-to-use medical device (e.g. catheter). This concentration corresponds to that obtained when all of the liquid is contacted with the liquid or solid hydrogen peroxide source.

Hydrogen peroxide is a well known substance that is degraded rapidly to water and oxygen in the body. Thus, hydrogen peroxide does not harm the human body when administered in low concentration. However, the fact that hydrogen peroxide may decompose fairly easily under conditions suitable for medical use may give rise to a stability problem when a medical device (e.g. a urinary catheter) with a coating of a porous polymer composition (e.g. a hydrophilic coating) is stored in contact with a liquid swelling medium containing hydrogen peroxide. This problem is particularly relevant to address when the medical device, after production, is intended to have a relatively long shelf-life, e.g. of more than a few months or even up to a year or more (see the Examples).

Packing Means

In view of the above-mentioned stability problems, the assembly of the present invention also comprises (iv) packing means that is adapted to hold (i) said medical device element(s), (ii) said liquid(s) and (iii) said hydrogen peroxide source in at least two separate compartments, i.e. the three items (i)-(ii) are not all in direct contact with each other when the packing means is in the defined configuration, i.e. the three items (i)-(iii) are in "at least two separate compartments".

Two separate compartments within the packing means may be arranged (i) so that a first compartment is adjacent to a second compartment; (ii) so that a second compartment is arranged within a first compartment, and vice versa; (iii) so that a first compartment and a second compartment are constituted by bags, ampoules, capsules, etc. arranged loosely within a third compartment of the packing means; etc. The skilled person will appreciate that other possible configurations are also encompassed.

In one embodiment of the packing means, said second compartment has sealing means adapted to release the hydrogen peroxide source into said first compartment as said sealing means is removed.

By the term "packing means" is meant a structure intended to enclose other objects, liquids, etc. so as to shield said objects, liquids, etc. from the exterior of the packing means.

Packing means may include plastics such as polyvinyl chloride (PVC), polyethylene (PE), polypropylene (PP), polyvinylidene difluoride (PVDF), polytetrafluoroethylene (PTFE), rubber such as e.g. synthetic caoutchouc-ethylene-propylene-diene-monomer (EPDM), FKM fluoroelastomer, and paper coated with such polymers and rubbers. Plastics and rubbers suitable for storage of hydrogen peroxide should be corrosion resistant and should not lead to degradation of hydrogen peroxide. The inner surfaces of the compartment containing hydrogen peroxide could also be coated with inert metals such as titanium and platinum.

Polyethylene is the currently preferred material for the inner lining of the compartment that comes in contact with the hydrogen peroxide source, because it reacts only slowly with hydrogen peroxide.

The part of the packing means constituting the compartment comprising hydrogen peroxide or a solution of hydrogen peroxide is in one embodiment made of multilayered materials in order to obtain gas impermeability (and possibly also opaqueness) so as to avoid any detrimental effects on the stability of hydrogen peroxide. This multilayered material can be a three-layered foil consisting of polyethyleneterephthlate (PET)/aluminium/polyethylene (PE), where polyethylene is the inner layer of the compartment that is in direct contact with the hydrogen peroxide or hydrogen peroxide-containing swelling medium.

The term "gas impermeable" should be understood in this context to mean any material that will be sufficiently tight against diffusion by evaporation of the liquid swelling medium for a period exceeding the recommended shelf life of the assembly which could be up to five years, typically about 36 months or more.

The packing means is preferably further adapted so as to allow establishment of contact between said medical device element(s), said liquid(s), and said hydrogen peroxide source.

Upon use of the assembly, one or both (or all) compartments are opened in such a manner that (i) said medical device element(s), (ii) said liquid(s) and (ill) said hydrogen peroxide source are contacted with the aim of providing the coating of the medical device element(s) with a liquid comprising hydrogen peroxide. Opening of the compartment(s) as outlined above may be accomplished by protruding the wall of one or both (or all) compartments, by breaking a seal, by twisting of a cap, etc. (see also below).

In a preferred variant, the constituents are allowed to become contacted with each other within the packing means, i.e. while packing means still envelope the constituents. In this way, the wetting of the coating of the medical device can be conducted under sterile conditions.

Figure 1B:
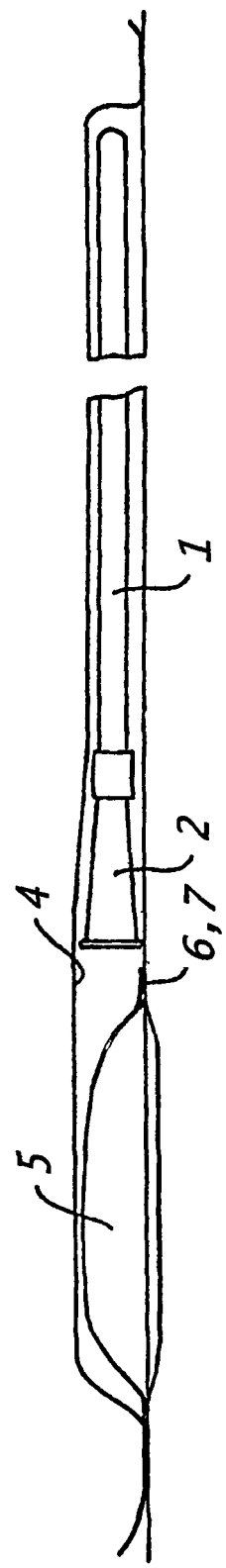

Many designs for the packing means can be envisaged, and examples of packing means suitable for this purpose are, e.g., disclosed in EP 0 923 398 and in WO 03/092779, and in FIGS. 1 and 2.

FIG. 1 illustrates an example of a packing means (3) with two separate compartments (4 and 5). The first compartment (4) holds a catheter consisting of two catheter elements (1 and 2), one of which (1) has a coating of a porous polymer composition. The second compartment (5) in the form of a pouch is arranged within the first compartment (4) and holds a liquid swelling medium (such as a hydrogen peroxide solution). The outlet part (6) of the pouch (5) is facing the catheter elements (1 and 2). The outlet part (6) is closed by a rupturable closure in the form of a welding (7) providing a relatively faint joint which will be ruptured upon application of pressure on the pouch (5). This can be done by squeezing the packing means (3) without actually opening the packing means. In this way, the wetting (swelling) of the catheter-element (1) can be effected under sterile conditions.

Figures 2A, 2B:
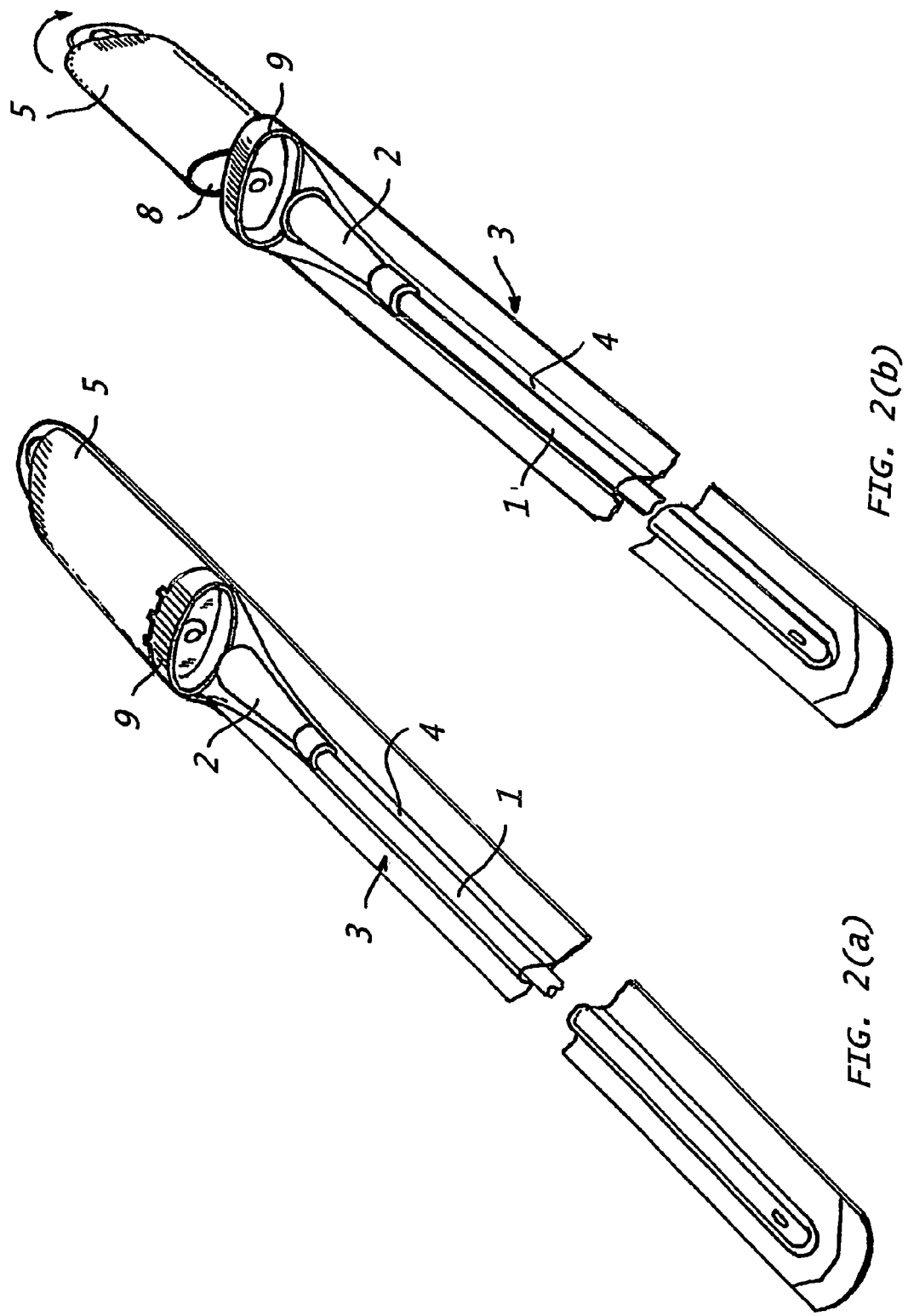

FIG. 2 illustrates another example of a packing means (3) with two separate compartments (4 and 5). The first compartment (4) holds a catheter consisting of two catheter elements (1 and 2), one of which (1) has a coating of a porous polymer composition. The second compartment (5) in the form of a rigid container is arranged adjacent to the first compartment (4) and holds a liquid swelling medium (such as a hydrogen peroxide solution). The end wall (8) of the rigid container (5) is facing the end wall (9) of the first compartment (4). As illustrated (FIG. 2(b)), the second compartment (5) is arranged to be turnable with respect to the end wall (9) of the first compartment (4) to bring liquid outlet and inlet openings provided in the end wall (8) and the end wall (9), respectively, into liquid flow alignment. The liquid swelling medium of the second compartment (5) can thereby be transferred to the first compartment (4), whereby the liquid swelling medium can enter the pores of the coating of the catheter element (1).

Examples of commercial products for which the present invention can be applied are assemblies of urinary hydrophilic coated catheters having an ampoule (a second compartment) with liquid swelling medium integrated within the product, e.g. "LoFric® H2O" supplied by Astra Tech AB and "EasiCath® Set" supplied by Coloplast A/S. In these products, the ampoule with the liquid swelling medium is separated from the dry, coated catheter. Prior to use, the ampoule is broken, and the liquid swelling medium is absorbed into the hydrophilic coating.

Various Embodiments of the Assembly

In one interesting embodiment of the assembly defined above, the polymer composition comprises a hydrophilic polymer forming a hydrophilic coating on at least a part of the surface of the medical device element(s), and the liquid(s) is/are liquid swelling medium/media.

In a further interesting embodiment, the medical device element(s) comprise(s) catheter element(s). More particularly, the medical device is a catheter such as a urinary catheter. In a preferred variant, at least a part of the catheter element has a hydrophilic coating adapted to reduce the friction and to introduce the hydrogen peroxide in a body opening, e.g. in the urethra.

In a currently most preferred embodiment, the assembly is a catheter assembly comprising (i) at least one catheter element with a hydrophilic coating covering at least a part of said catheter element(s), (ii) at least one swelling medium for swelling said hydrophilic coating, (iii) a hydrogen peroxide source, and (iv) packing means, said packing means being adapted to hold said catheter element(s), said swelling medium/media and said hydrogen peroxide source in at least two separate compartments.

In one embodiment thereof, the packing means is adapted to establish contact between the catheter element(s), the swelling medium/media and the hydrogen peroxide source, e.g. as outlined above.

The invention will primarily be described with reference to the "catheter" embodiment and the "hydrophilic coating"

embodiment in the following, but it should be understood that the guidelines given are equally applicable for other embodiments of the invention.

In one main embodiment of the catheter assembly, a first compartment of the packing means is adapted to hold a catheter element and a second compartment of the packing means is adapted to hold a hydrogen peroxide source. The hydrogen peroxide source may be a solid provided as one or more pills or a powder, or a liquid solution of hydrogen peroxide may be provided as at least a part of the liquid swelling medium, which is added to the catheter element(s) prior to use.

A preferred embodiment of the above is the one wherein a first compartment of said packing means is adapted to hold the catheter element(s), and wherein a second compartment of said packing means is adapted to hold at least a part of the liquid swelling medium and the hydrogen peroxide source. When present in the same compartment, i.e. in the second compartment, the liquid swelling medium and the hydrogen peroxide source typically form an aqueous hydrogen peroxide solution, i.e. the second compartment holds a solution of hydrogen peroxide in at least a part of the liquid swelling medium. Thus, in this embodiment, the hydrogen peroxide source is hydrogen peroxide in an aqueous solution.

In one variant of the above, the first compartment of the packing means holds at least a part of the liquid swelling medium, i.e. the catheter element is at least partly swelled with the liquid swelling medium, whereas another part of the liquid swelling medium is combined with the hydrogen peroxide. This has the advantage that the catheter element(s) may be provided in a pre-swelled condition. In this variant, however, it is important to ensure that a suitable portion of the hydrogen peroxide-containing swelling medium is allowed to enter the hydrophilic coating.

In another variant of the above, the second compartment of the packing means holds the entire amount of the liquid swelling medium, i.e. the catheter element(s) is/are present in the first compartment in substantially "dry" form.

Thus, in one particularly interesting variant, the first compartment of said packing means is adapted to hold the catheter element(s), and the second compartment of said packing means is adapted to hold the entire amount of the liquid swelling medium and hydrogen peroxide, i.e. the second compartment holds an aqueous hydrogen peroxide solution.

Irrespective of the selection of the above embodiments, the content of the liquid (e.g. liquid swelling medium/media) and the hydrogen peroxide source in the assembly are preferably selected so that the concentration of hydrogen peroxide in the liquid (swelling medium) will be in the range of 0.01-5.0% (w/w), such as 0.1-3.0% (w/w), such as 0.2-2.0% (w/w) when the liquid (swelling medium) and hydrogen peroxide are present in the pores of the polymer composition (e.g. has swelled the hydrophilic coating). In the embodiment where a second compartment of the packing means holds a solution of hydrogen peroxide in the entire liquid swelling medium, the before-mentioned concentrations of course correspond to those in such an aqueous solution.

In the above embodiments, where a second compartment of the packing means holds a solution of hydrogen peroxide in at least a part of the liquid swelling medium, it may be fairly relevant for the manufacturer of the assembly to ensure that the concentration of hydrogen peroxide is maintained at a constant level even after storage for many months or even years under varying conditions with respect to temperature and light exposure. Thus, the solution of hydrogen peroxide in at least a part of the liquid swelling medium preferably includes a stabilizer.

More particularly, the present inventors have identified a preference for embodiments where the solution of hydrogen peroxide in the liquid swelling medium is an aqueous solution of hydrogen peroxide further comprising one or more constituents selected from stabilizer(s), buffer(s), and osmolality increasing agent(s), in particular at least a stabilizer.

Examples of stabilizers (most typically selected among chelators that are added to bind metal ions which otherwise tend to enhance decomposition of hydrogen peroxide) are deferoxamine, polysaccharides, gelatine, acetate, citrate, EDTA and corresponding salts, diethylenetriaminepentaacetic acid (DETAPAC) and corresponding salts, ethylenediaminetetra(methylenephosphonic acid) (EDATMP) or corresponding salts, diethylenetriaminepenta (methylenephosphonic acid) (DETAPMP) or corresponding salts, 1-hydroxyethane-1,1-diphosphonic acid (HEDP) or corresponding salts, gluconate, orthophosphate, pyrophosphate, triphosphate, hexametaphosphate, phytate, sorbitol, tartrate, silicates (such as colloidal silicate), colloidal stannate, sodium pyrophosphate, and organophosphonates. Preferred examples are EDTA, gelatine, deferoxamin, polysaccharides, and diethylenetriaminepentaacetic acid (DETAPAC). In a further preferred embodiment of the invention, said chelator is DETAPMP or deferoxamin, a polyhydroxamic acid which is also known as desferrioxamine.

The content of stabilizer(s) in the aqueous solution of hydrogen peroxide is typically in the range of 0-2000 mg/L, and more typically 25-1200 mg/L.

Examples of buffers are citrate, acetate, glycolate, phosphate, benzoates, amino acids, formiate, oxalate, malonate, succinate, glutarate, adipate, malate, lactate, sulfanilates, borates, bicarbonate, sulfate, and similar substances.

The content of buffer(s) in the aqueous solution of hydrogen peroxide is typically in the range of 0-200 mM, and more typically 0-50 mM, e.g. up to 50 mM such as 2-50 mM.

Examples of osmolality increasing agents are alkali metal (e.g. lithium, sodium, potassium, etc.) and earth alkali metal (magnesium, calcium, etc.) nitrates, alkali metal and earth alkali metal sulfates, alkali metal and earth alkali metal chlorides, glycine, glycerol and urea. An osmolality increasing agent is not strictly necessary, but it is often relevant in order to improve the comfort during use of the medical device.

The content of osmolality increasing agent(s) in the aqueous solution of hydrogen peroxide is typically in the range of 0-1000 mM, and more typically 0-300 mM, e.g. up to 300 mM such as 5-300 mM.

It is envisaged that the aqueous solution of hydrogen peroxide may comprise minor amounts of other constituents not explicitly mentioned hereinbefore. The content of such "other constituents" is typically 0-2000 mg/L, such as 0-500 mg/L.

Typically, the aqueous solution has a pH in the range of 2.0-8.5, preferably in the range of 3.0-5.0.

In one embodiment, the aqueous solution of hydrogen peroxide comprises:
 0.01-5.0% (w/w) of hydrogen peroxide,
 0-2000 mg/L of one or more stabilizers,
 0-200 mM of one or more buffers,
 0-1000 mM osmolality increasing agents,
 and has a pH in the range of 2.0-8.5.

In another embodiment, the aqueous solution of hydrogen peroxide comprises:
 0.01-5.0% (w/w) of hydrogen peroxide,
 25-1200 mg/L of one or more stabilizers,
 0-25 mM of one or more buffers,
 0-300 mM osmolality increasing agents,
 and has a pH in the range of 2.0-8.5.

In still another embodiment, the aqueous solution of hydrogen peroxide consists of:
0.1-3.0% (w/w) of hydrogen peroxide,
25-1200 mg/L of one or more stabilizers,
0-10 mM of one or more buffers,
0-300 mM osmolality increasing agents,
0-2000 mg/L of other constituents, and
the balance of pure water,
and has a pH in the range of 2.0-8.5.

In a currently most preferred embodiment, the aqueous solution of hydrogen peroxide consists of:
0.3-2% (w/w) of hydrogen peroxide,
25-1200 mg/L of a stabilizer, preferably selected from the group consisting of DETAPMP and deferoxamine,
0-300 mM sodium sulfate or sodium nitrate as osmolality increasing agent,
0-2000 mg/L of other constituents, and
the balance of pure water,
and has a pH in the range of 2.0-8.5.

pH is typically adjusted with sodium hydroxide and sulfuric acid or nitric acid as required.

The above-defined aqueous solutions are particularly preferred for the embodiments where the second compartment holds the entire liquid swelling medium.

In view of the before-mentioned swelling media, the present invention also provides a liquid swelling medium corresponding to the above embodiment for the "aqueous solution of hydrogen peroxide", which is useful for swelling a hydrophilic coating. In particular, the present invention provides an antimicrobial liquid swelling medium comprising:
0.01-5.0% (w/w) of hydrogen peroxide,
25-1200 mg/L of one or more stabilizers,
0-25 mM of one or more buffers,
0-300 mM osmolality increasing agents,
and has a pH in the range of 2.0-8.5.

In a different embodiment, the packing means of the catheter assembly contains at least one hydrogen peroxide source in solid form. In this embodiment, a first compartment of the packing means preferably holds at least one hydrogen peroxide source and at least one catheter element. More particularly, a first compartment of the packing means is adapted to hold the catheter element(s) and the solid hydrogen peroxide source. Preferably, a second compartment of the packing means is adapted to hold the liquid swelling medium/media.

The solid hydrogen peroxide source may be in the form of a powder, one or more pills, one or more tablets, capsules, pearls, or a coating or film on the inner side of said first compartment, or the hydrogen peroxide source is incorporated in the catheter element(s), e.g. as clots embedded in the hydrophilic coating, a layer in the coating or as a layer on top of the coating. Upon use, the liquid swelling medium is added and the hydrogen peroxide source is dissolved in said liquid swelling medium or reacts with the liquid swelling medium to release hydrogen peroxide and hydrogen peroxide is swelled into the hydrophilic coating.

In a variant of this embodiment, a solid hydrogen peroxide source is included in the coating of the catheter element as molecules entrapped in the pores of the hydrophilic coating or as part of at least one compound used to make the hydrophilic coating. In one variant thereof, the solid hydrogen peroxide source comprises hydrogen peroxide complexed with polyvinylpyrrolidone (PVP). In particular, at least a part of said hydrophilic coating is prepared from a polyvinylpyrrolidone (PVP)-hydrogen peroxide compound.

In this embodiment, the chemical cross-linkage or assembly of polymer molecules into the polymer composition is conducted in the presence of the hydrogen peroxide resulting in entrapment of the hydrogen peroxide. The hydrogen peroxide may either be present in a free form or be part of or complexed to one of the ingredients participating in, or required for, the chemical cross-linkage process. For example, a polymer composition could contain a polymer capable of forming a complex with hydrogen peroxide such as PVP or related polymers.

Hydrogen peroxide initially complexed to such a polymer may later be cross-linked to a matrix, to form e.g. a hydrophilic coating.

In a still further embodiment of the catheter assembly, the packing means comprises a first compartment adapted to hold the catheter element(s), a second compartment adapted to hold the liquid swelling medium and a third compartment adapted to hold the hydrogen peroxide source.

In a preferred variant hereof, the catheter assembly comprises a packing means adapted for automatic release of the hydrogen peroxide source to the liquid swelling medium as the packing means is opened. This can be obtained by having the compartment with hydrogen peroxide and the compartment with liquid swelling medium separated by a foil membrane that is broken as the packaging is opened.

Preferred Embodiment

In a currently most preferred embodiment, the present invention provides a catheter assembly comprising (i) at least one catheter element with a hydrophilic coating covering at least a part of said catheter element(s), said hydrophilic coating comprising cross-linked polyvinylpyrrolidone, (ii) at least one liquid swelling medium for swelling said hydrophilic coating, and (iv) packing means, said packing means having a first compartment to hold said catheter element(s) and a second compartment to hold said liquid swelling medium, said liquid swelling medium having the following composition:
0.1-3.0% (w/w) of hydrogen peroxide,
25-1200 mg/L of one or more stabilizers,
0-10 mM of one or more buffers,
0-300 mM osmolality increasing agents,
0-2000 mg/L of other constituents, and
the balance of pure water,
and has a pH in the range of 2.0-8.5.

An Assembly Comprising Further or Alternative Anti-Microbial Agents

Irrespective of the fact that the above-mentioned assemblies define hydrogen peroxide as an advantageous anti-microbial agent, it is envisaged that one or more other anti-microbial agents may be used in the liquid (swelling medium) in connection with hydrogen peroxide, or as alternatives to hydrogen peroxide. Examples of such further or alternative anti-microbial agents are silver sulfadiazine, silver hydantoinate, silver 5,5-dimethylhydantoinate, polymeric silver imidazolate, silver chloride, silver sodium thiosulfate (SST), silver thiosalicylate, silver tris complex, polyvinylpyrrolidone-iodine (povidone-iodine, PVP-$I_2$), benzalkonium chloride, Bronopol (2-bromo-2-nitro-1,3-propanediol), Kathon (80:20 mixture of 5-chloro-2-methyl-4-isothiazolin-3-one and 2-methyl-4-isothiazolin-3-one), phenyl salicylate, zinc chloride, copper chloride, hexamethylenetetramine, diazolidinyl urea, mandelic acid, hippuric acid, chloramine T, chloramine B, chlorhexidine digluconate, chlorhexidine dihydrochloride, and nitrofurazone. The currently most interesting anti-microbial agents are benzalkonium chloride, silver sulfadiazine, silver hydantoinate, silver 5,5-dimethylhydantoinate and polymeric silver imidazolate, in particular benzalkonium chloride.

Thus, the above-mentioned aspects and embodiments of the assembly (e.g. catheter assembly) are also relevant for the combination of one or more of such anti-microbial agents with hydrogen peroxide.

Furthermore, the above-mentioned aspects and embodiments of the assembly (e.g. catheter assembly) are also relevant for such alternative anti-microbial agents used alone or in combination with each other, i.e. without the presence of hydrogen peroxide, mutatis mutandis.

Preparation of Assemblies

The assemblies of the present invention are typically prepared by simple combination of conventional methods for the preparation of medical devices with porous coatings (in particular hydrophilic coatings), liquids for medical uses, and packing means for medical devices.

Thus, in the embodiment wherein a first compartment of said packing means is adapted to hold the catheter element(s), and wherein a second compartment of said packing means is adapted to hold the liquid swelling medium and the hydrogen peroxide source, the assembly can be prepared by a method comprising the steps: preparation of the liquid swelling medium by combining the relevant constituents (see elsewhere herein); preparation of the catheter element(s) using conventional techniques; arrangement of the catheter element(s) in the first compartment of the packing means (possibly including welding of the compartment wall); arrangement of the liquid swelling means in the second compartment of the packing means (possibly including welding to the compartment wall); and possibly sterilization of the assembly, e.g. by irradiation.

In the event where sterilization by irradiation is effected for an assembly wherein an element has a hydrophilic coating comprising at least a part of the liquid swelling medium, it may be advantageous to modify the liquid swelling medium by incorporation of 0.3-10% of a hydrophilic polymer, e.g. a low molecular weight hydrophilic polymer (Mw 1500-50,000), as disclosed by the applicant in EP 0 935 478 (see also Example 1 herein). Examples of useful hydrophilic polymers are PVP C-15 (ISP) and PVP K-12 (BASF).

The preparation of the packing means and actual selection of materials will be known by the person skilled in the art.

Use of the Assembly and the Medical Device

The assembly defined above is suitably used for making ready-to-use a medical device such as a catheter. The content of the first, second, and possibly further, compartments are brought together whereby the liquid and/or hydrogen peroxide are allowed to enter the pores of the polymer composition. In one embodiment, an aqueous solution of hydrogen peroxide (e.g. a hydrogen peroxide-containing swelling medium) is allowed to swell a coating of a hydrophilic polymer.

For the exemplary packing means illustrated in FIGS. 1 and 2, this can be done as described above under the detailed description of said figures.

After preparation of the ready-to-use medical device, the medical device can be used in the conventional way, i.e. the user or medical practitioner should normally not take any particular measures or make any deviations compared to the conventional way of utilizing the medical device.

In the case of a urinary catheter, the catheter (or a catheter element) is inserted into the urethra or an artificial urethral opening and thereby introduces hydrogen peroxide in the urethral opening, i.e. a concentration of hydrogen peroxide that will provide an inhibiting effect on at least some microbes such as vira, bacteria, fungi or mold. A part of the anti-microbial effect may be obtained by direct contact of the medical device with the urethra, and after the device has been removed an effect may be present due to deposition of a part of the coating and/or the liquid in the urethra. Part of the effect during and after catheterization may also be due to efflux of the hydrogen peroxide from the coating.

By having the hydrogen peroxide in the entire coating, it is in each instance assured that bacteria located at all sites in the urethra will be exposed to an efficient dose/concentration of the hydrogen peroxide and thereby killed or inhibited. Also the risk of infection related to contamination (from fingers, surroundings) by handling of the catheter before insertion will be reduced before or during use of the catheter as the entire catheter element surface has anti-microbial activity.

Novel Medical Devices

As it will be clear from the above, the present invention provides an assembly which is useful for providing a ready-to-use medical device. It is believed that some medical devices resulting from the assembly of the invention are novel as such.

Thus, the present invention also provides a medical device having on at least a part of the surface thereof a coating of a porous polymer composition, wherein said coating comprises a liquid that comprises hydrogen peroxide and an agent that stabilizes hydrogen peroxide.

Most typically, the concentration of hydrogen peroxide in said liquid in said coating is in the range of 0.01-5.0% (w/w), such as 0.1-3.0% (w/w), such as 0.2-2.0% (w/w).

Useful examples of agents that stabilize hydrogen peroxide are those defined above as "stabilizers". The liquid may further comprise buffers, osmolality increasing agents, and have an adjusted pH, in particular as described hereinabove.

In one preferred embodiment, the coating of a porous polymer composition is a hydrophilic coating of at least one hydrophilic polymer, and the liquid is a liquid swelling medium for said hydrophilic polymer. The hydrophilic coating/polymer is preferably selected as described hereinabove. Preferably, at least one hydrophilic polymer is polyvinylpyrrolidone. More preferably, at least one of the hydrophilic polymer(s) is cross-linked.

Examples of liquid swelling media suitable for hydrophilic coatings, in particular cross-linked polyvinylpyrrolidone coatings, are the ones mentioned above as embodiment for the "aqueous solutions of hydrogen peroxide". For example, the liquid swelling medium is one comprising:

0.01-5.0% (w/w) of hydrogen peroxide,
25-1200 mg/L of one or more stabilizers,
0-25 mM of one or more buffers,
0-300 mM osmolality increasing agents,
and has a pH in the range of 2.0-8.5.

In some particularly interesting embodiments, the medical device is a catheter such as a urinary catheter.

Other Aspects

The present invention also provides a method of treatment, alleviation or prophylaxis of microbial infections wherein a medical device, in a first step, is prepared from the assembly defined herein and, in a second step, is brought into contact with a body part of a mammal (such as a human) in need for said medical device.

Also, the present invention provides a method of treatment, alleviation or prophylaxis of microbial infections wherein a medical device as defined herein is brought into contact with a body part of a mammal (such as a human) in need for said medical device.

Particularly relevant microbial infections are those causing urinary tract infections (UTI). Thus, particularly relevant medical devices for the above aspects are catheters, especially urinary catheters, where the number of incidences of urinary tract infections is reduced. It is believed that this result is obtained because the number of bacteria in the urine, urethra and/or urethral meatus is reduced when the assembly and urinary catheter of the invention is utilized instead of a conventional urinary catheter.

Alternative Aspects

An Assembly of a Medical Device Having a Coating Comprising a Liquid with Hydrogen Peroxide Although the present inventors currently have a preference for the embodiments where the medical device element(s) (e.g. the catheter element(s)), the swelling medium/media and the hydrogen peroxide source(s) are accommodated in at least two separate compartments, it also envisaged that the beneficial properties of hydrogen peroxide can be utilised for an assembly comprising (i) a medical device (e.g. a catheter) having a coating (e.g. a hydrophilic coating) in which a liquid is present, and wherein said liquid comprises hydrogen peroxide, and (ii) a packing means which is adapted to hold the medical device in a compartment thereof. Such a medical device may be useful due to the fact that it is immediately ready-to-use, although the assembly only may have a moderate, but for some applications still satisfactory, shelf-life.

Thus, the present inventors also provide an assembly comprising (i) at least one medical device element having a coating of a porous polymer composition, said coating covering at least a part of said element(s), and said coating having present therein a liquid comprising hydrogen peroxide, and (ii) packing means adapted to hold said medical device element(s). Preferably, the medical device element(s) is/are held in one compartment of the packing means.

Most typically, the concentration of hydrogen peroxide in said liquid in said coating is in the range of 0.01-5.0% (w/w), such as 0.1-3.0% (w/w), such as 0.2-2.0% (w/w).

For certain applications where a relatively long shelf-life is desirable, it is advantageous to further include an agent that stabilizes hydrogen peroxide in the liquid. Useful examples of agents that stabilize hydrogen peroxide are those defined above as "stabilizers". The liquid may further comprise buffers, osmolality increasing agents, and have an adjusted pH, in particular with the possibilities and ranges described hereinabove.

Preferably, the polymer composition comprises at least one hydrophilic polymer. Hydrophilic polymers may be used e.g. in hydrophilic coatings intended to provide a low friction surface of a medical device, such as a urinary catheter.

In the event where sterilization of the assembly by irradiation is desirable, it is advantageous to modify the liquid swelling medium by incorporation of 0.3-10% of a hydrophilic polymer, e.g. a low molecular weight hydrophilic polymer (Mw 1500-50,000), as disclosed by the applicant in EP 0 935 478 (see also Example 1 herein). Examples of useful hydrophilic polymers are PVP C-15 (ISP) and PVP K-12 (BASF).

In one preferred embodiment, the coating of a porous polymer composition is a hydrophilic coating of at least one hydrophilic polymer, and the liquid is a liquid swelling medium for said hydrophilic polymer. The hydrophilic coating/polymer is preferably selected as described hereinabove. Preferably, at least one hydrophilic polymer is polyvinylpyrrolidone. More preferably, at least one of the hydrophilic polymer(s) is cross-linked.

More particularly, the present invention relates to a urinary catheter having on at least a part of the surface thereof a hydrophilic coating of a hydrophilic polymer (in particular cross-linked polyvinylpyrrolidone), wherein said coating comprises a liquid swelling medium that comprises hydrogen peroxide and, optionally, an agent that stabilizes hydrogen peroxide, said catheter being held in a compartment of a packing means.

In this embodiment, the aqueous hydrogen peroxide solution is typically introduced to the polymer composition immediately after the chemical cross-linking of the hydrophilic polymer. More generally, the medical device carrying the coating of the polymer composition can be submerged into an aqueous hydrogen peroxide solution. The hydrogen peroxide solution may then diffuse into the polymer composition by either a passive process, or may be forced into the coating by application of pressure.

Examples of liquid swelling media suitable for hydrophilic coatings, in particular cross-linked polyvinylpyrrolidone coatings, are the ones mentioned above as embodiment for the "aqueous solutions of hydrogen peroxide", but preferably (in particular where sterilization by irradiation is desirable) modified by the incorporation of 0.3-10% of a hydrophilic polymer as described above. For example, the liquid swelling medium is one comprising:

0.01-5.0% (w/w) of hydrogen peroxide,
optionally, but preferably, 0.3-10% of a hydrophilic polymer,
0-2000 mg/L of one or more stabilizers,
0-200 mM of one or more buffers,
0-1000 mM osmolality increasing agents,
and has a pH in the range of 2.0-8.5.
or one comprising:
0.01-5.0% (w/w) of hydrogen peroxide,
optionally, but preferably, 0.3-10% of a low molecular weight hydrophilic polymer,
25-1200 mg/L of one or more stabilizers,
0-25 mM of one or more buffers,
0-300 mM osmolality increasing agents,
and has a pH in the range of 2.0-8.5.

The medical device may be prepared following the directions hereinabove with respect to the medical device, the porous polymer composition and the liquid/liquid swelling medium comprising hydrogen peroxide, and can then be packed in a suitable packing means.

In some particularly interesting embodiments, the medical device is a catheter such as a urinary catheter. An example of a commercially available urinary catheter coated with a hydrophilic polymer where the coated catheter is in contact with the swelling medium is "SpeediCath®" supplied by Coloplast A/S.

A further aspect of the above is a method of treatment, alleviation or prophylaxis of microbial infections wherein a medical device of an assembly as defined above is brought into contact with a body part of a mammal (such as a human) in need for said medical device.

EXAMPLES

Example 1

Preparation of Catheters Coated with Polyvinylpyrrolidone

A urinary catheter having a hydrophilic coating of polyvinylpyrrolidone can be prepared according to the following steps:

a) Preparation of a first and a second solution of polyvinylpyrrolidone (PVP) with a high molecular weight (e.g. Plasdone K-90) dissolved in a solvent/plasticizer mixture of N-methylpyrrolidone (NMP), ethanol and Citrofol A1 including a photoinitiator. The solutions have a content of PVP in the range of 1-8% (w/w). Possibly, the first and the second solution is the same.

b) Dipping a polyurethane raw catheter in the first solution and letting it dry at ambient temperature for 10-120 seconds.

c) Dipping the resulting catheter in the second solution of PVP.

d) Further drying the catheter at elevated temperature (e.g. at 70-80° C.).

e) Cross-linking the PVP by exposing the coated catheter to UV-light having a wavelength range between 200 nm and 300 nm for ½-15 minutes.

f) Arranging the cross-linked coated catheter in a packing means and filling of the packaging with the swelling medium, where the swelling medium is an aqueous solution of low molecular PVP (Plasdone C15) and an osmolality increasing agent (NaCl).

g) Sterilization of the packing means comprising the wetted catheter by ionizing irradiation (β- or γ-irradiation).

Example 2

Preparation of Catheters Comprising Hydrogen Peroxide

The preparation of a sterilized catheter having a hydrophilic coating comprises steps of:

a) Preparation of a first and a second solution of polyvinylpyrrolidone (PVP) with a high molecular weight (e.g. Plasdone K-90) dissolved in a solvent/plasticizer mixture of N-methylpyrrolidone (NMP), ethanol and Citrofol A1 including a photo-initiator. The solutions have a content of PVP in the range of 1-8% (w/w). Possibly, the first and the second solution is the same.

b) Dipping a polyurethane raw catheter in the first solution and letting it dry at ambient temperature for 10-120 seconds.

c) Dipping the resulting catheter in the second solution of PVP.

d) Further drying the catheter at elevated temperature (e.g. at 70-80° C.)

e) Cross-linking the PVP by exposing the coated catheter to UV-light having a wavelength range between 200 nm and 300 nm for ½-15 minutes.

f1) Placing the cross-linked coated catheter in a packaging and filling of the packaging with the swelling medium, where the swelling medium is an aqueous solution of hydrogen peroxide, low molecular PVP (Plasdone C15) and an osmolality increasing agent ($Na_2SO_4$ or $NaNO_3$) and a stabilizer (DETAPMP); and g1) Sterilization of the packing means comprising the wetted catheter by ionizing irradiation (β- or γ-irradiation).
or f2) Placing the cross-linked coated catheter in one compartment of a packing means and placing the swelling medium in a second compartment, where the swelling medium is an aqueous solution of hydrogen peroxide, osmolality increasing agent(s) (e.g. $Na_2SO_4$ or $NaNO_3$) and a stabilizer (DETAPMP); and g2) Sterilization of the packing means comprising the coated catheter in a dry state (compartment 1) and the hydrogen peroxide solution (compartment 2) by ionizing irradiation (β- or γ-irradiation).

Example 3

Preparation of a Catheter Assembly

A catheter assembly as illustrated in FIG. 2 can be prepared as follows:

A dry urinary catheter coated with polyvinylpyrrolidone (PVP) (1) is prepared as described in Example 1. The catheter is arranged in the first compartment (4) of the packing means (3), which is sealed by welding. A liquid swelling medium containing an aqueous solution of hydrogen peroxide, DETAPMP and an osmolality increasing agent (e.g. $Na_2SO_4$ or $NaNO_3$) is prepared (e.g. as outlined in Example 2) and loaded into the second compartment formed by an external rigid container (5) arranged as an integrated part of the packing means (3). As illustrated in FIG. 2(b), the container (5) is arranged to be turnable through approx. 90° with respect to the end wall (8) to bring liquid outlet and inlet openings provided in the end wall (8) of the container (5) facing the rigid end wall (9) of the compartment (4), respectively, into liquid flow alignment, whereby the content of the liquid swelling medium in the container (5) can be transferred to the first compartment holding the coated catheter.

In a variant, the coated urinary catheter is pre-swelled by providing a portion of a liquid swelling medium (preferably an aqueous solution of low molecular weight PVP and $Na_4SO_4$) to the first compartment (4) before sealing the compartment by welding. Upon use, the two swelling media are combined by allowing the content of the container (5) flow into the first compartment. Hence, the two swelling media are instantly mixed (e.g. by tipping the package end-to-end 2-10 times before use) whereby the coating will absorb the swelling medium comprising hydrogen peroxide, preferably within 30 sec. The catheter is then ready to use.

Example 4

Storage of One-Compartment $H_2O_2$ Catheter with PEG 2000 in Swelling Medium

An experiment was conducted to establish the effect of storage temperature, initial $H_2O_2$ concentration and PEG 2000 on pH, degradation of $H_2O_2$, and friction of a catheter with a hydrophilic coating. The catheter was prepared as described in Example 2 and the swelling medium was prepared from pure water, hydrogen peroxide (see Table 1.1), PEG 2000 (as specified in Table 1.1) and further contained 50 mM citrate buffer at pH 5.5. The catheter and swelling medium were packed together in one single compartment as outlined in Example 2, and were stored at 60° C. or 80° C. for one week. 1-3 unsterilized samples were used for each determination. The results are shown in Table 1.1.

TABLE 1.1

| Initial %-point $H_2O_2$ | Storage temperature | 6% PEG 2000 present? | Friction (N) | pH after storage | Appearance of catheter (0–5; 0 = perfect, 5 = unacceptable) | Appearance of swelling medium (0–5) | %-point $H_2O_2$ after storage | Loss of $H_2O_2$ (%/day) |
|---|---|---|---|---|---|---|---|---|
| 0.2 | 60 | — | 0.06 | 5.64 | 0 | 0 | 0.20 | 0.3 |
| 0.4 | 60 | — | 0.10 | 5.63 | 0 | 0 | 0.37 | 1.0 |

TABLE 1.1-continued

| Initial %-point $H_2O_2$ | Storage temperature | 6% PEG 2000 present? | Friction (N) | pH after storage | Appearance of catheter (0–5; 0 = perfect, 5 = unacceptable) | Appearance of swelling medium (0–5) | %-point $H_2O_2$ after storage | Loss of $H_2O_2$ (%/day) |
|---|---|---|---|---|---|---|---|---|
| 0.8 | 60 | — | 0.27 | 5.63 | 0 | 0 | 0.75 | 0.9 |
| 1.6 | 60 | — | 0.53 | 5.71 | 0 | 0 | 1.41 | 1.7 |
| 1.6 | 60 | Yes | 0.12 | 5.13 | 1 | 0 | 1.25 | 3.2 |
| 0.2 | 80 | — | 1.06 | 5.63 | 0 | 0 | 0.15 | 3.5 |
| 0.4 | 80 | — | 1.15 | 5.79 | 0 | 0 | 0.29 | 3.8 |
| 0.8 | 80 | — | 1.26 | 5.86 | 0 | 0 | 0.58 | 4.0 |
| 1.6 | 80 | — | 1.02 | 6.28 | 0 | 0 | 1.13 | 4.2 |
| 1.6 | 80 | Yes | 1.68 | 3.46 | 3 | 0 | 0.02 | 14.1 |

At 60° C. the friction of the catheters and the relative breakdown of $H_2O_2$ increased with the initial $H_2O_2$ concentration when no PEG 2000 was added. pH increased marginally from the initial value of 5.5, probably because of the $HO^-$-producing Fenton reaction:

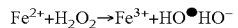

$$Fe^{2+} + H_2O_2 \rightarrow Fe^{3+} + HO^\bullet HO^-$$

This indicated that $H_2O_2$ attacked the catheter during storage, although the appearance of both catheters and swelling media were perfect (score 0 on the appearance scale).

When PEG 2000 was added, the friction of the catheters was much lower after storage (0.12 N) than without PEG 2000 (0.53 N), but at the same time pH dropped to 5.13, the catheters became milky and opaque (score 1), and the loss of $H_2O_2$ was 3.2%/day or almost twice as high as at the same start concentration of $H_2O_2$ (1.6%-point) but without PEG 2000 (loss 1.7%/day). It seemed that PEG 2000 was oxidized by $H_2O_2$ to carboxylic acids capable of lowering the pH and complexing with PVP to produce the opaque coating.

At 80° C. all catheters had frictions higher than 1 N, so the coating had been severely damaged. The samples without PEG 2000 had slightly higher pH after storage at 80° C. than after storage at 60° C. 25-30% of the $H_2O_2$ disappeared during storage for 1 week at 80° C. of samples not containing PEG 2000, regardless of the initial $H_2O_2$ concentration.

When 6% PEG 2000 was added, virtually all $H_2O_2$ had disappeared after storage for 1 week, and pH fell abruptly to 3.46 in spite of the presence of 50 mM citrate buffer. The frictions were as high as in samples without PEG 2000, and the catheters became very opaque (score 3).

These observations demonstrate that $H_2O_2$ can attack the catheter both with and without PEG 2000 present. Hence, the long term stability of a package with a hydrophilic catheter and a $H_2O_2$-containing swelling medium in the same compartment may be compromised.

Example 5

Storage of One-Compartment $H_2O_2$ Catheter with PVP C-15 in Swelling Medium

A reduced factorial experiment was conducted to find, among other things, the storage stability of 1%-point $H_2O_2$ in a liquid swelling medium without buffer at pH 7 in the presence or absence of PVP C-15 instead of PEG 2000. Samples were β-sterilized at 50 kGy and stored at 23° C. for 8 months.

The concentration of $H_2O_2$ at day 0 after sterilization was taken as 100%, and the degradation rate (%/day) was calculated, assuming a linear breakdown profile. For example, if the $H_2O_2$ concentration had dropped to 75% after 8 months (about 250 days), the degradation rate was 25/250%/day=0.1%/day.

The results were calculated from 86 separate samples (mean value±standard deviation of mean value) (Table 5.1).

TABLE 5.1

| Initial % $H_2O_2$ | % PVP C-15 | β-sterilization dose (kGy) | Storage temperature | $H_2O_2$ loss per day (%) |
|---|---|---|---|---|
| 1 | 0 | 50 | 23 | 0.088 ± 0.029 |
| 1 | 6 | 50 | 23 | 0.167 ± 0.048 |

The degradation rate was higher in the presence of PVP C-15 in the swelling medium than without PVP C-15 present. A similar trend was noted at other storage temperatures (5° C., 40° C., 60° C.).

Example 6

Effect of Chelators on Stabilization of $H_2O_2$

Chelators and/or metal ions were added to an aqueous solution of hydrogen peroxide and then stored. Table 6.1 below shows %-point hydrogen peroxide remaining after 24 days storage at 40° C. of β-sterilized (50 kGy) polyurethane catheters with hydrophilic coating in a swelling medium initially consisting of 1%-point hydrogen peroxide, 1 g/L chelator (EDTA, DETAPAC, deferoxamine, gelatin) or no chelator, 10 mg/L metal ion ($Fe^{2+}$, $Cu^{2+}$) or no metal ion, 6% PVP K-12, and 10 mM citrate (pH 7).

TABLE 6.1

%-point remaining hydrogen peroxide remaining after 24 days storage at 40° C.

| | 1000 mg/L chelator | | | | |
|---|---|---|---|---|---|
| 10 mg/L metal ion | EDTA | DETAPAC | Gelatine | Deferoxamine | None |
| Cu(2+) | 0.37 | 0.44 | 0.30 | 0.31 | 0.15 |
| Fe(2+) | 0.29 | 0.46 | 0.25 | 0.66 | 0.28 |
| None | 0.59 | 0.61 | 0.60 | 0.68 | 0.59 |

At 10 mg/L $Cu^{2+}$ the concentration of hydrogen peroxide decreased from 1%-point to 0.15%-point after storage when no chelator was added. Each of the four chelators improved the stability of hydrogen peroxide considerably, so 0.30-0.44%-point hydrogen peroxide remained after storage.

With 10 mg/L $Fe^{2+}$ added, DETAPAC and deferoxamine improved the stability of hydrogen peroxide. In particular, the effect of deferoxamine was so great that the stability of $H_2O_2$ with added $Fe^{2+}$ was just as good (0.66%-point $H_2O_2$ remaining after storage) as when no $Fe^{2+}$ was added (0.68%-point $H_2O_2$ remaining). That is, deferoxamine completely inactivated $Fe^{2+}$. Furthermore, deferoxamine was the only chelator that improved the fundamental stability of hydrogen peroxide when no metal ions were added: 0.68%-point $H_2O_2$ remained after storage with deferoxamine, whereas only 0.59-0.61%-point $H_2O_2$ remained when the 3 other chelators were added or no chelator was added.

Hence deferoxamine and other chelators had a beneficial effect on the storage stability of hydrogen peroxide.

Example 7

Influence of β-Sterilization on Degradation of Hydrogen Peroxide

The objective of this series of experiments was to investigate the influence of increasing irradiation doses on the degradation of hydrogen peroxide. Furthermore it was the purpose to look into the role of the catheter and PVP on the stability of hydrogen peroxide.

Hydrogen peroxide 33% Panreac Ph.Eur, BP, REF. (14.1077.14.10)

Citric acid-1-hydrate, Riedel-de Haên

Plasdone C-15, ISP 0.02 M $KMnO_4$, Riedel de Haën

Brown 50 mL PE-containers $H_2O_2$-concentrations are measured by potentiometric titration using $KMnO_4$.

Titrino 702 titrator (Metrohm).

Two 1.0 L swelling media were produced; a solution containing distilled water and 1% hydrogen peroxide, and a solution of 6% PVP, 10 mM citric acid and 1% hydrogen peroxide. The pH value of the latter solution was adjusted to 5.5 with 1 M NaOH. 10.0 mL aliquots of each of the two solutions were taken out and placed in 50 mL brown PE-containers.

The samples were β-irradiation at Risø National Laboratory. The samples were measured before irradiation, immediately after irradiation and after 2 and 4 weeks storage at 60° C. (triple determination). The results are shown in Tables 7.1-7.3.

TABLE 7.1

Catheter swelled in a solution of PVP (Series I). Concentration of $H_2O_2$ (%-point). Mean value (n = 3).

| Dose of irradiation | After irradiation | 1 week at 60° C. | 2 weeks at 60° C. |
| --- | --- | --- | --- |
| 0 kGy | 1.00 | 0.97 | 0.87 |
| 25 kGy | 0.85 | 0.79 | 0.70 |
| 50 kGy | 0.73 | 0.58 | 0.46 |
| 75 kGy | 0.57 | 0.37 | 0.26 |

TABLE 7.2

Catheter swelled in distilled water (Series II). Concentration of $H_2O_2$ (%-point). Mean value (n = 3).

| Dose of irradiation | After irradiation | 1 week at 60° C. | 2 weeks at 60° C. |
| --- | --- | --- | --- |
| 0 kGy | 1.00 | 0.98 | 0.92 |
| 25 kGy | 0.93 | 0.91 | 0.85 |
| 50 kGy | 0.87 | 0.81 | 0.75 |
| 75 kGy | 0.81 | 0.74 | 0.66 |

TABLE 7.3

$H_2O_2$-solution in distilled water (Series III). Concentration of $H_2O_2$ (%-point). Mean value (n = 3).

| Dose of irradiation | After irradiation | 1 week at 60° C. | 2 weeks at 60° C. |
| --- | --- | --- | --- |
| 0 kGy | 1.00 | 0.87 | 0.76 |
| 25 kGy | 0.95 | 0.91 | 0.88 |
| 50 kGy | 0.92 | 0.84 | 0.85 |
| 75 kGy | 0.89 | 0.79 | 0.77 |

Increasing irradiation doses resulted in increasing degradation for Series I. The correlation between increasing irradiation doses and increasing degradation of hydrogen peroxide was not as evident for Series II and III, but there was a tendency that a higher irradiation dose caused a higher degradation rate.

Furthermore it can be seen that Series I had higher degradation rates than Series II and III, meaning that PVP dissolved in distilled water increased the degradation of hydrogen peroxide. From this study it could not be concluded that the catheter in itself influenced the stability of hydrogen peroxide.

Example 8

Degradation of Hydrogen Peroxide vs. Concentration of Stabilizer

The objective of this study was to determine the concentration of the stabilizer DETAPMP that resulted in the most stabile solution of $H_2O_2$. A further objective was to determine the activation energy for the degradation of $H_2O_2$ containing the stabilizer DETAPMP at pH 4 and 10 mM citrate.

Materials

Citric acid-1-hydrate. Reag. ACS, Reag. ISO

NaOH 4 M, Merck

HCl 1 M, BHD AnalR Volumetric Solution

NaCl (Extra pure, Ph. Eur, BP, USP)

0.02 M $KMnO_4$, Riedel de Haën

Potentiometric titration Titrino 702, Metrohm

Methods

Degradation Rates of $H_2O_2$ in Solutions Containing DETAPMP at 40° C., 50° C. and 60° C.

1 L swelling medium was produced containing 10 mM citrate, 500 g/mL stabilizer DETAPMP and 0.7% NaCl. The pH-value of the solution was adjusted to pH 4 with 4 M NaOH and 1 M HCl.

Dose-Response Profile for Stabilizer DETAPMP

Seven swelling media were produced. Each swelling medium contained 10 mM citrate, 0.7% NaCl and stabilizer DETAPMP (50, 100, 150, 200, 250, 350, 500 mg/L).

20 mL aliquots of each of the swelling media were taken out and added to each of the stick-packs. The stick-packs were closed by welding after filling and sent off to irradiation at Risø National Laboratory. The irradiation dose was 2*26 kGy.

The stick-pack with "peel" was a laminated material consisting of PETP (12 μm), aluminium (9 μm) and polyethylene peel (polyethylene+10% polybutylene) (70 μm). The stick-packs were made out of a stamped area of 13×35 mm that was welded in the longitudinal direction by 1×3 units on a welder. It was welded by 2×2.2 units across in one end of the stick-pack, and in the other end by 4.0 bar, 130° C. and 3.5 s (breakable seal).

Results and Discussion

The results of the study are shown in Tables 8.1 and 8.2

TABLE 8.1

Degradation rates for a 1% $H_2O_2$ containing DETAPMP at different temperatures

| Storage temperature | Rate constant (k) (%/day) | log k (%/day) |
|---|---|---|
| 40° C. | 0.0932 | −1.031 |
| 50° C. | 0.1722 | −0.764 |
| 60° C. | 0.3691 | −0.433 |

An Arrhenius plot for the stabilizer DETAPMP at 40° C., 50° C. and 60° C. (DETAPMP at pH 4 and 10 mM citrate) showed a virtually linear relationship between 1/T and log k and revealed that the activation energy for the degradation of $H_2O_2$ was 59.6 kJ/mol. An activation energy of 59.6 kJ/mol resulted in a $Q_{10} \approx 2$, which meant that the degradation rate increased by 2 for each 10° C.

TABLE 8.2

Concentration of $H_2O_2$ (%) after storage at 40° C. for 7 different concentrations of DETAPMP (mg/L).

| Days | 50 | 100 | 150 | 200 | 250 | 350 | 500 |
|---|---|---|---|---|---|---|---|
| 0 | 0.92 | 0.91 | 0.91 | 0.91 | 0.90 | 0.91 | 0.91 |
| 14 | 0.89 | 0.89 | 0.90 | 0.89 | 0.89 | 0.89 | 0.89 |
| 25 | 0.89 | 0.88 | 0.89 | 0.89 | 0.89 | 0.89 | 0.89 |

Table 8.2 shows the correlation between the concentration of stabilizer and degradation rate of $H_2O_2$ it could be surmised that the reaction rate of degradation of $H_2O_2$ decreased for DETAPMP concentrations up to about 150-200 mg/L. After that there was a levelling of the curve. However, the smallest degradation of $H_2O_2$ was seen at 250 mg/L DETAPMP.

Example 9

Various Stabilizers

The objective of this study was to identify the stabilizer that gave the most stabilized solution of hydrogen peroxide. It is well known from the literature that the pH-value influences the stability of hydrogen peroxide. Therefore the investigation of the influence of the pH-value on the stability in our system was included in the study. The packaging material was also investigated to see whether two different kinds of material affected the degradation of hydrogen peroxide in different ways.

Citric acid-1-hydrate. Reag. ACS, Reag. ISO
4 M NaOH, Merck
1 M HCl, BHD AnalR Volumetric Solution
NaCl (Extra pure, Ph. Eur, BP, USP)
0.02 M $KMnO_4$, Riedel de Haën
pH-Meter, Jenway 4330 Conductivity and pH-meter
Potentiometric titration Titrino 702, Metrohm
The chemical name and CAS No. of the stabilizers:
DETAPMP-sodium salt (Sodium salt of Diethylenetriaminepenta(methylenephosphonic)acid; 22042-96-2),
EDATMP (Ethylenediaminetetra(methylenephosphonic)acid; 1429-50-1),
HEDP (1-Hydroxyethane-1,1 diphosphonic acid; 2809-21-4),
EDATMP-sodium salt (Sodium salt of Ethylenediaminetetra(methylenephosphonic)acid; 15142-96-8),
DETAPMP (Diethylenetriaminepenta(methylenephosphonic)acid; 15827-60-8),
Acetanilide (103-84-4).

24 different kinds of swelling media containing different stabilizers (one without stabilizer) and 3 different pH-values (pH 4, 5.5 and 7) were prepared. The volume of each of the swelling media was 1 L and the initial concentration of hydrogen peroxide was approx. 1% (w/w). Furthermore, swelling media containing the stabilizer DETAPMP and sodium chloride at three different pH-values were produced to see the effect of an addition of sodium chloride. The concentration of sodium chloride in each of these three swelling media was 0.7% (w/w). Sodium chloride was tested because it could be used as an osmolality increasing agent. Citric acid was added to each of the swelling media to reach a concentration of 25 mM, so that the initial pH-value was maintained throughout the period of testing. Finally the pH-value of the solutions were adjusted to 4.0, 5.5 and 7.0 by adding 4 M NaOH and 1 M HCl to the final solution.

20 mL aliquots of each of the swelling media were taken out and added to each of the stick-packs. Two different kinds of material for the stick-pack were used, one with "peel" and one with "non-peel". The stick-packs were closed by welding after filling and sent off to irradiation at Risø National Laboratory. The irradiation dose was 2*26 kGy.

The stick-pack with "peel" was a laminated material consisting of PETP (12 µm), aluminium (9 µm) and polyethylene peel (polyethylene+10% polybutylene) (70 µm). The stick-pack with "non-peel" was a laminated material consisting of PETP (12 µm), aluminium (9 µm) and polyethylene (PE) (50 µm). The stick-packs were made out of a stamped area of 13×35 mm that was welded in the longitudinal direction by 1×3 units on a welder. It was welded by 2×2.2 units across in one end of the stick-pack, and in the other end by 4.0 bar, 130° C. and 3.5 s (breakable seal).

The stick-packs were stored for stability testing at 23° C. and 40° C. Samples were taken out after irradiation and after 2 and 4 weeks at 40° C. and 8 and 16 weeks at 23° C. The pH-value and the concentration of hydrogen peroxide were measured (duplicate determinations), see Table 9.1.

TABLE 9.1

The calculated amount of degraded $H_2O_2$ after 2 years of storage at 23° C. The calculations were based on degradation studies at 23° C. for up to 18 weeks.

| pH | DETAPMP | DETAPMP + NaCl | Sodium salt of DETAPMP | EDATMP |
|---|---|---|---|---|
| 4 | 5.3% | 13.5% | 27.5% | 22.2% |
| 5.5 | 17.6% | 13.5% | 18.0% | 30.9% |
| 7 | 15.3% | 12.9% | 29.2% | 173.3% |

| pH | HEDP | Sodium salt of EDATMP | Acetanilide | No stabilizer |
|---|---|---|---|---|
| 4 | 65.4% | 18.3% | 21.2% | 15.7% |
| 5.5 | 150.0% | 14.5% | 21.4% | 31.7% |
| 7 | 351.1% | 25.8% | 20.2% | 54.7% |

From the results it can be seen that the most stable solution of $H_2O_2$ was obtained in a solution containing stabilizer DETAPMP at pH 4. In general there was a tendency towards higher degradation at pH 7 than at pH 4. It may also be seen that stabilizer EDTMP and HEDP actually increased the degradation of $H_2O_2$ especially at pH 7 compared to the solutions of $H_2O_2$ without stabilizers.

Further experiments (data not shown) demonstrated that the two different kind of packaging, i.e. "peel" vs. "non-peel", did not differ in their influence on the degradation of $H_2O_2$.

Finally, it was shown that the degradation at pH 4 was higher for DETAPMP+NaCl than for DETAPMP alone. This could indicate that NaCl increased the degradation of hydrogen peroxide.

Example 10

Effect of Buffer in Swelling Medium

The objective of this study was to clarify the effect of the buffer (citrate) at different pH-values on the degradation rate of hydrogen peroxide and to verify that the use of the stabilizer DETAPMP resulted in the most stable solution of hydrogen peroxide.

Citric acid-1-hydrate. Reag. ACS, Reag. ISO
NaOH 4 M, Merck
HCl 1 M, BHD AnalR Volumetric Solution
NaCl (Extra pure, Ph. Eur, BP, USP)
0.02 M $KMnO_4$, Riedel de Haën
Potentiometric titration Titrino 702, Metrohm The swelling media contained approx. 1% (w/w) hydrogen peroxide; 0, 10 and 25 mM citrate, and 0.7% (w/w) NaCl and stabilizers. The pH-value of the solutions were adjusted with 4 M NaOH and 1 M HCl. The concentrations of the stabilizers were DETAPMP (500 mg/L), sodium salt of EDATMP (500 mg/L, 1000 mg/L) and sodium salt of DETAPMP (1000 mg/L).

10 mL aliquots of each swelling medium was taken out and added to each of the stick-packs (with "peel"; see Example 7). The stick-packs were closed by welding after filling and sent off to irradiation at Risø National Laboratory. The irradiation dose was 2*26 kGy. The results are shown in Tables 10.1-10.6.

TABLE 10.1

0 mM citrate. Calculated degraded amount of $H_2O_2$ (%) after 2 years storage at 23° C.

|  | pH 4 | pH 5.5 | pH 7 |
| --- | --- | --- | --- |
| DETAPMP | 8.4 | 28.0 | 18.2 |
| Sodium salt of DETAPMP | 16.8 | 22.4 | 26.6 |
| Sodium salt of EDATMP-500 mg/L | 15.4 | 18.2 | 35.0 |
| Sodium salt of EDATMP 1000 mg/L | 15.4 | 21.0 | 25.2 |
| No stabilizer | 15.4 | 22.4 | 60.2 |

TABLE 10.2

10 mM citrate. Calculated degraded amount of $H_2O_2$ (%) after 2 years storage at 23° C.

|  | pH 4 | pH 5.5 | pH 7 |
| --- | --- | --- | --- |
| DETAPMP | 23.8 | 29.4 | 19.6 |
| Sodium salt of DETAPMP | 22.4 | 26.6 | — |
| Sodium salt of EDATMP-500 mg/L | 19.6 | 53.2 | 86.8 |
| Sodium salt of EDATMP 1000 mg/L | 37.8 | 30.8 | 43.4 |
| No stabilizer | 47.6 | 63.0 | 277.1 |

TABLE 10.3

25 mM citrate. Calculated degraded amount of $H_2O_2$ (%) after 2 years storage at 23° C.

|  | pH 4 | pH 5.5 | pH 7 |
| --- | --- | --- | --- |
| DETAPMP | 25.2 | 42.0 | 32.2 |
| Sodium salt of DETAPMP | 33.6 | 30.8 | 29.4 |
| Sodium salt of EDATMP-500 mg/L | 50.4 | 103.6 | 137.1 |
| Sodium salt of EDATMP 1000 mg/L | 50.4 | 39.2 | 158.1 |
| No stabilizer | 39.2 | 74.2 | 201.5 |

TABLE 10.4 pH 4. Calculated degraded amount of $H_2O_2$ (%) after 2 years storage at 23° C.

|  | 0 mM citrate | 10 mM citrate | 25 mM citrate |
| --- | --- | --- | --- |
| DETAPMP | 8.4 | 23.8 | 25.2 |
| Sodium salt of DETAPMP | 16.8 | 22.4 | 33.6 |
| Sodium salt of EDATMP-500 mg/L | 15.4 | 19.6 | 50.4 |
| Sodium salt of EDATMP 1000 mg/L | 15.4 | 37.8 | 50.4 |
| No stabilizer | 15.4 | 47.6 | 39.2 |

TABLE 10.5 pH 5.5. Calculated degraded amount of $H_2O_2$ (%) after 2 years storage at 23° C.

|  | 0 mM citrate | 10 mM citrate | 25 mM citrate |
| --- | --- | --- | --- |
| DETAPMP | 28.0 | 29.4 | 42.0 |
| Sodium salt of DETAPMP | 22.4 | 26.6 | 30.8 |
| Sodium salt of EDATMP-500 mg/L | 18.2 | 53.2 | 103.6 |
| Sodium salt of EDATMP 1000 mg/L | 21.0 | 30.8 | 39.2 |
| No stabilizer | 22.4 | 63.0 | 74.2 |

TABLE 10.6 pH 7. Calculated degraded amount of $H_2O_2$ (%) after 2 years storage at 23° C.

|  | 0 mM citrate | 10 mM citrate | 25 mM citrate |
| --- | --- | --- | --- |
| DETAPMP | 18.2 | 19.6 | 32.2 |
| Sodium salt of DETAPMP | 26.6 | — | 29.4 |
| Sodium salt of EDATMP-500 mg/L | 35.0 | 86.8 | 137.1 |
| Sodium salt of EDATMP 1000 mg/L | 25.2 | 43.4 | 158.1 |
| No stabilizer | 60.2 | 277.1 | 201.5 |

It may be seen that increasing the pH-value from 4 to 5.5 and 7 increased the degradation rate for nearly all of the solutions. There was also a correlation between increasing amounts of citrate in the solution and increased degradation rate of $H_2O_2$. The most stable solution of $H_2O_2$ contained stabilizer DETAPMP, no added citrate and an initial pH-value of the solution of 4. Increasing the amount of the stabilizer sodium salt of EDATMP did not result in a more stable solution. Apparently there was no correlation between increasing stability of $H_2O_2$ and increasing concentration of the sodium salt of EDATMP.

Example 11

Anti-Microbial Potency of Hydrogen Peroxide

Effect of Different Concentrations of Hydrogen Peroxide on the Bacterial Growth Rate The data show the capability of 7 different bacterial strains to proliferate in the presence or absence of hydrogen peroxide (range 0-1%). In brief, the bacteria were inoculated in growth medium with or without hydrogen peroxide and the growth at the mid-log phase was measured by the absorbance at 600 nm. The obtained data from each specific bacterial strain were pooled. The data are mean values from 3 independent experiments, each determination done in duplicate; see Table 11.1.

TABLE 11.1

| % Hydrogen Peroxide | Mean (% of control) | SD |
|---|---|---|
| 0 (control) | 100.0 | — |
| 0.00000256 | 110.0 | 8.1 |
| 0.0000128 | 99.8 | 2.8 |
| 0.000064 | 97.9 | 6.0 |
| 0.000320 | 96.2 | 6.7 |
| 0.0016 | 87.3 | 11.2 |
| 0.008 | 63.0 | 28.2 |
| 0.04 | 35.6 | 18.6 |
| 0.2 | 16.0 | 10.6 |
| 1.0 | 11.7 | 8.2 |

Effect of Different Concentrations of Hydrogen Peroxide on the Bacterial Survival Rate The data show the capability of 7 different bacterial strains to survive in the presence or absence of hydrogen peroxide (range 0-1%). The bacteria were exposed to the hydrogen peroxide for 60 min., see Table 11.2.

TABLE 11.2

| % Hydrogen Peroxide | Mean | SD |
|---|---|---|
| 0 (control) | 100.0 | — |
| 0.016 | 49.8 | 4.1 |
| 0.031 | 38.1 | 12.4 |
| 0.063 | 27.8 | 16.1 |
| 0.125 | 14.5 | 8.4 |
| 0.250 | 9.1 | 6.1 |
| 0.500 | 0.2 | 0.2 |
| 1.000 | 0.0 | 0.5 |

Time Course Effect of 1% Hydrogen Peroxide on the Bacterial Survival Rate

The data shows the capability of 7 different bacterial strains to survive in the presence of 1% hydrogen peroxide. The number of surviving bacteria (% of control) was determined after 0, 5, 10, and 15 min., see Table 11.3.

TABLE 11.3

| Exposure time (min) | Mean (% of control) | SD |
|---|---|---|
| 0 (control) | 100 | — |
| 5 | 37 | 31 |
| 10 | 17 | 18 |
| 15 | 6 | 7 |

Example 12

Alternative Antimicrobial Agents

A series of antibacterial agents (See Table 12.1) were swelled into a hydrophilic coating on urinary catheters. The catheters were stored about 0, 3, 6 and 12 weeks at 25° C., 40° C., and 60° C. Agar plates were inoculated with various bacterial strains clinically isolated from infected human urine, and added the coated catheter on top of the surface of the agar. The agar plates were incubated for 18 hours at 37° C., and visually tested for presence or absence of an inhibition zone.

Catheter sections with a hydrophilic coating were swelled with a solution of the anti-microbial agents and were placed on agar plates inoculated with bacteria (clinical isolates, − and + denotes Gram positive and or Gram negative, respectively): *Proteus mirabilis* (−), *Pseudomonas aeruginosa* (−), *E. coli* (−), *Providencia Stuartii* (−), *Staphylococcus aureus* (+), *Enterococcus faecalis* (+) and *Klebsielia* (−).

A highly fractionated factorial design ($2^{15-10}_{IV}$-design) was constructed by Design Expert software (version 6.0.6) and used to screen 32 of the $2^{15}$=32768 possible combinations, where each compound was either absent or present in a relevant concentration. Each mixture further contained 50 mM citrate buffer at pH 5.5, 160 mM NaCl and 6% PEG 2000. All samples were β-sterilized with a dose of 50 kGy. The constituents and concentrations of the 32 solutions are described in Table 12.1:

TABLE 12.1

| Std | Hexamethylenetetramin A g/L | Diazolidinyl urea B g/L | Mandelic acid C g/L | Hippuric acid D g/L | Chloramine T E g/L | PVP-I2 F g/L | Chlorhexidine digluconate, 20% G g/L | Benzalkonium chloride H g/L | Bronopol J g/L | Kathon K g/L | Phenyl salicylate L g/L | Hydrogen peroxide M g/L | Zinc chloride N g/L | Copper chloride O g/L | Silver chloride P mg |
|---|---|---|---|---|---|---|---|---|---|---|---|---|---|---|---|
| 1 | 0 | 0 | 0 | 0.6 | 0 | 0 | 0.65 | 1 | 1 | 0 | 0 | 1 | 0 | 1 | 20 |
| 2 | 0 | 1 | 1 | 0.6 | 0 | 0 | 0 | 0 | 1 | 0.094 | 0.02 | 1 | 0 | 0 | 0 |
| 3 | 0 | 1 | 0 | 0 | 1 | 10 | 0.65 | 0 | 1 | 0 | 0.02 | 1 | 0 | 0 | 20 |
| 4 | 0 | 1 | 1 | 0.6 | 1 | 0 | 0 | 0 | 1 | 0 | 0 | 0 | 1 | 1 | 20 |
| 5 | 1 | 1 | 1 | 0 | 0 | 10 | 0 | 0 | 0 | 0 | 0 | 1 | 0 | 0 | 20 |
| 6 | 0 | 0 | 0 | 0.6 | 1 | 0 | 0.65 | 1 | 1 | 0.094 | 0.02 | 0 | 1 | 0 | 0 |
| 7 | 0 | 0 | 1 | 0.6 | 0 | 10 | 0.65 | 0 | 0 | 0 | 0.02 | 1 | 1 | 1 | 0 |
| 8 | 1 | 1 | 0 | 0.6 | 1 | 0 | 0.65 | 0 | 0 | 0.094 | 0 | 1 | 0 | 1 | 0 |
| 9 | 1 | 1 | 1 | 0 | 1 | 10 | 0 | 0 | 0 | 0.094 | 0.02 | 0 | 0 | 0 | 0 |
| 10 | 0 | 1 | 0 | 0.6 | 1 | 10 | 0 | 1 | 0 | 0 | 0.02 | 0 | 0 | 1 | 0 |

TABLE 12.1-continued

| Std | Hexamethylenetetramin A g/L | Diazolidinyl urea B g/L | Mandelic acid C g/L | Hippuric acid D g/L | Chloramine T E g/L | PVP-12 F g/L | Chlorhexidine digluconate, 20% G g/L | Benzalkonium chloride H g/L | Bronopol J g/L | Kathon K g/L | Phenyl salicylate L g/L | Hydrogen peroxide M g/L | Zinc chloride N g/L | Copper chloride O g/L | Silver chloride P mg |
|---|---|---|---|---|---|---|---|---|---|---|---|---|---|---|---|
| 11 | 1 | 1 | 0 | 0 | 0 | 0 | 0 | 1 | 1 | 0 | 0.02 | 1 | 1 | 1 | 0 |
| 12 | 0 | 0 | 0 | 0 | 1 | 0 | 0 | 0 | 0 | 0.094 | 0.02 | 1 | 1 | 1 | 20 |
| 13 | 1 | 1 | 1 | 0.6 | 1 | 10 | 0.65 | 1 | 1 | 0.094 | 0.02 | 1 | 1 | 1 | 20 |
| 14 | 0 | 0 | 0 | 0 | 0 | 0 | 0 | 0 | 0 | 0 | 0 | 0 | 0 | 0 | 0 |
| 15 | 0 | 1 | 1 | 0 | 0 | 0 | 0.65 | 1 | 0 | 0.094 | 0.02 | 0 | 0 | 1 | 20 |
| 16 | 1 | 1 | 1 | 0.6 | 0 | 10 | 0.65 | 1 | 1 | 0 | 0 | 0 | 0 | 0 | 0 |
| 17 | 1 | 0 | 1 | 0 | 1 | 0 | 0.65 | 0 | 1 | 0 | 0.02 | 0 | 0 | 1 | 0 |
| 18 | 0 | 1 | 0 | 0.6 | 0 | 10 | 0 | 1 | 0 | 0.094 | 0 | 1 | 1 | 0 | 20 |
| 19 | 1 | 1 | 0 | 0.6 | 0 | 0 | 0.65 | 0 | 1 | 0 | 0.02 | 0 | 1 | 0 | 20 |
| 20 | 0 | 1 | 0 | 0 | 0 | 10 | 0.65 | 0 | 1 | 0.094 | 0 | 0 | 1 | 1 | 0 |
| 21 | 1 | 1 | 0 | 0 | 1 | 0 | 0 | 1 | 1 | 0.094 | 0 | 0 | 0 | 0 | 20 |
| 22 | 1 | 0 | 1 | 0.6 | 0 | 0 | 0 | 1 | 0 | 0.094 | 0 | 0 | 1 | 1 | 0 |
| 23 | 1 | 0 | 0 | 0.6 | 0 | 10 | 0 | 0 | 1 | 0.094 | 0.02 | 0 | 0 | 1 | 20 |
| 24 | 0 | 0 | 1 | 0.6 | 1 | 10 | 0.65 | 0 | 0 | 0.094 | 0 | 0 | 0 | 0 | 20 |
| 25 | 1 | 0 | 1 | 0.6 | 1 | 0 | 0 | 1 | 0 | 0 | 0.02 | 1 | 0 | 0 | 20 |
| 26 | 0 | 1 | 1 | 0 | 1 | 0 | 0.65 | 1 | 0 | 0 | 0 | 1 | 1 | 0 | 0 |
| 27 | 1 | 0 | 1 | 0 | 0 | 0 | 0.65 | 0 | 1 | 0.094 | 0 | 1 | 1 | 0 | 20 |
| 28 | 1 | 0 | 0 | 0 | 0 | 10 | 0.65 | 1 | 0 | 0.094 | 0.02 | 1 | 0 | 0 | 0 |
| 29 | 0 | 0 | 1 | 0 | 0 | 10 | 0 | 1 | 1 | 0 | 0.02 | 0 | 1 | 0 | 20 |
| 30 | 0 | 0 | 1 | 0 | 1 | 10 | 0 | 1 | 1 | 0.094 | 0 | 1 | 0 | 1 | 0 |
| 31 | 1 | 0 | 0 | 0 | 1 | 10 | 0.65 | 1 | 0 | 0 | 0 | 0 | 1 | 1 | 20 |
| 32 | 1 | 0 | 0 | 0.6 | 1 | 10 | 0 | 0 | 1 | 0 | 0 | 0 | 1 | 1 | 0 |

Many of the 32 mixtures had powerful action against several of the 7 bacteria (0=no effect; 3=excellent effect), see Table 12.2 (sorted by decreasing antibacterial effect).

TABLE 12.2

| Std | P. Mirabilis | P. Aeruginosa | E. Coli | P. Stuartii | S. Aureus | E. Faecalis | Klebsiella |
|---|---|---|---|---|---|---|---|
| 3 | 3 | 3 | 3 | 3 | 3 | 3 | 3 |
| 32 | 3 | 3 | 3 | 3 | 3 | 3 | 3 |
| 29 | 3 | 3 | 3 | 3 | 3 | 3 | 2 |
| 19 | 3 | 3 | 3 | 2 | 2 | 3 | 3 |
| 21 | 2 | 3 | 3 | 3 | 3 | 3 | 3 |
| 20 | 2 | 2 | 3 | 2 | 3 | 3 | 3 |
| 10 | 2 | 2 | 2 | 3 | 3 | 3 | 3 |
| 11 | 2 | 2 | 2 | 3 | 2 | 3 | 2 |
| 5 | 2 | 1 | 1 | 1 | 2 | 3 | 2 |
| 13 | 1 | 3 | 1 | 1 | 3 | 3 | 1 |
| 16 | 1 | 3 | 2 | 2 | 2 | 3 | 1 |
| 24 | 1 | 0 | 2 | 0 | 2 | 3 | 3 |
| 6 | 1 | 3 | 1 | 2 | 2 | 3 | 3 |
| 14 | 1 | 1 | 1 | 1 | 2 | 3 | 1 |
| 30 | 1 | 0 | 0 | 0 | 2 | 3 | 3 |
| 25 | 1 | 3 | 2 | 2 | 1 | 3 | 2 |
| 18 | 1 | 3 | 2 | 1 | 1 | 3 | 2 |
| 28 | 1 | 2 | 1 | 1 | 1 | 3 | 1 |
| 17 | 1 | 0 | 1 | 1 | 1 | 1 | 1 |
| 23 | 1 | 3 | 1 | 0 | 1 | 3 | 3 |
| 22 | 1 | 3 | 0 | 1 | 0 | 3 | 3 |
| 31 | 1 | 0 | 0 | 0 | 0 | 0 | 0 |
| 7 | 0 | 3 | 2 | 2 | 2 | 3 | 3 |
| 2 | 0 | 3 | 1 | 2 | 2 | 3 | 3 |
| 15 | 0 | 0 | 1 | 1 | 2 | 3 | 1 |
| 12 | 0 | 2 | 1 | 0 | 2 | 1 | 1 |
| 9 | 0 | 2 | 1 | 1 | 1 | 3 | 1 |
| 4 | 0 | 1 | 1 | 1 | 0 | 3 | 1 |
| 8 | 0 | 1 | 0 | 1 | 0 | 0 | 1 |
| 1 | 0 | 0 | 0 | 1 | 0 | 0 | 0 |
| 26 | 0 | 0 | 0 | 0 | 0 | 0 | 1 |
| 27 | 0 | 0 | 0 | 0 | 0 | 0 | 0 |
| Sum | 35 | 58 | 44 | 44 | 51 | 77 | 59 |

When the results were analyzed and further tests were carried out to confirm the results, it appeared that the effects might be third-order interactions or higher. That is, the effects came from mixtures of 3, 5, 7 or any other odd number of compounds but apparently not from main effects or 2-factor interactions. Thus, a large synergistic action between the compounds appeared to be present. Chlorhexidine and silver chloride were sparingly soluble in media with 160 mM chloride; they may work better in chloride-free media.

Further experiments showed that the effect of hydrogen peroxide (taken alone) was rapid as compared to a range of other anti-microbial agents. This is an advantage in applications such as intermittent catheterization, which takes a few minutes only. In other experiments hydrogen peroxide showed a good efflux from the coating so that the treatment was extended to tissue at some distance from the coating. As a further advantage of using hydrogen peroxide the chances that some microbes may develop resistance to hydrogen peroxide are small.

Example 13

Silver Compounds 0.3 g/L silver sulfadiazine, 0.25 g/L silver hydantoinate, 1.175 g/L silver 5,5-dimethylhydantoinate, and 0.25 g/L polymeric silver imidazolate had a moderate to excellent antibacterial effect at pH 5.5 (50 mM citrate buffer), pH 7 (50 mM phosphate buffer) and pH 8.5 (50 mM TAPS buffer). The solutions further contained 160 mM NaCl and 6% PEG 2000, and all solutions were sterilized with 50 kGy β- or γ-irradiation. β-Irradiation generally gave a better antibacterial effect and a smaller degree of coloration of the products than γ-irradiation, so β-irradiation was the preferred sterilization method. The silver compounds only worked when excess undissolved salt was allowed in the packaging, that is, they had no antibacterial effect when they were decanted from their precipitate. In some experiments 0.01% $H_2O_2$ was added to prevent silver ions from being reduced to elemental silver, because this caused loss of antibacterial activity and strong coloration from colloidal silver.

The antibacterial effect of each compound was scored on a scale from 0 (no effect) to 3 (excellent effect) for each of the seven bacteria. The antibacterial index was defined as 5/12 multiplied by the sum of the square roots of the scores of each of the seven bacteria. Thus, the antibacterial index was a rational number between 0 and 5.05.

The appearance index was a weighted average of the subjective acceptability after sterilization of catheters packed in one single compartment with catheter and swelling medium (on a scale from 0 to 5: 0=totally unacceptable, e.g. by strong color or major precipitation; 5=perfect, e.g. no coloration, no precipitate) of the hydrophilic catheter (weighted 60%) and the swelling medium (weighted 40%). Hence the appearance index was a number between 0 and 5.

The antibacterial index and appearance index of the silver compounds is shown in Table 13.1.

The antibacterial index and appearance index of the silver compounds may be seen here, ordered by antibacterial index (5,5-DMH=5,5-dimethylhydantoinate):

TABLE 13.1

| Silver compound | pH | 0.01% $H_2O_2$ added? | Anti-bacterial index | Appearance index |
|---|---|---|---|---|
| Imidazolate, pH 5.5 | 5.5 | No | 0.8 | 3.4 |
| 5,5-DMH/pH 5.5/$H_2O_2$ | 5.5 | Yes | 1.4 | 5 |
| 5,5-DMH, pH 8.5 | 8.5 | No | 1.7 | 2.2 |
| 5,5-DMH, pH 5.5 | 5.5 | No | 1.8 | 2.8 |
| Hydantoinate/5.5/$H_2O_2$ | 5.5 | Yes | 2.3 | 3.6 |
| Imidazolate/pH 5.5/$H_2O_2$ | 5.5 | Yes | 2.7 | 3 |
| Hydantoinate, pH 5.5 | 5.5 | No | 2.7 | 4 |
| Imidazolate, pH 8.5 | 8.5 | No | 2.8 | 3.2 |
| Sulfadiazine, pH 8.5 | 8.5 | No | 2.9 | 2.8 |
| Sulfadiazine, pH 7.0 | 7 | No | 3.1 | 2.8 |
| Sulfadiazine, pH 5.5 | 5.5 | No | 3.1 | 3.6 |
| Hydantoinate, pH 8.5 | 8.5 | No | 3.2 | 2.8 |
| Sulfadiazine/pH 5.5/$H_2O_2$ | 5.5 | Yes | 3.2 | 3 |
| Imidazolate, pH 7.0 | 7 | No | 3.2 | 4.2 |
| Hydantoinate, pH 7.0 | 7 | No | 3.3 | 3.4 |
| 5,5-DMH, pH 7.0 | 7 | No | 3.4 | 3.4 |

Hence silver compounds with precipitate had a good antibacterial effect even in media containing 160 mM NaCl, which decreased the solubility of the compounds drastically. Even better results should be obtained in chloride-free media.

Example 14

Benzalkonium Chloride 1-5 g/L benzalkonium chloride in 50 mM citrate (pH 5.5), 160 mM NaCl and 6% PEG 2000 had a moderate to high antibacterial effect on *E. faecalis, Klebsiella, S. aureus, E. coli, P. stuartii* and *P. aeruginosa*, but not *P. mirabilis*. Hence benzalkonium chloride may also be used for antibacterial catheters.

The invention claimed is:

1. A catheter assembly comprising
   (i) at least one catheter element with a hydrophilic coating covering at least a part of said element,
   (ii) at least one liquid for swelling said hydrophilic coating,
   (iii) an aqueous solution of hydrogen peroxide in at least a portion of said liquid for swelling, said aqueous solution of hydrogen peroxide having a pH value of from 3.0 to 5.0 and including a stabilizer that is a chelator, and
   (iv) a packing structure having a first compartment that holds said catheter element and a second compartment that releasably holds at least said aqueous solution of hydrogen peroxide, said aqueous solution of hydrogen peroxide being releasably contained in said second compartment so as to be separate from said first compartment, and said first compartment holds at least another portion of said liquid for swelling.

2. The catheter assembly according to claim 1, wherein said aqueous solution of hydrogen peroxide includes one or more constituents selected from the group consisting of buffers and osmolality increasing agents.

3. The catheter assembly according to claim 2, wherein said aqueous solution of hydrogen peroxide includes:
   0.01-5.0% (w/w) of said hydrogen peroxide;
   25-1200 mg/L of said stabilizer;
   0-25 mM of said one or more buffers; and
   0-300 mM of said osmolality increasing agents.

4. The catheter assembly according to claim 1, wherein said hydrophilic coating includes a cross-linked polyvinylpyrrolidone, and said aqueous solution of hydrogen peroxide includes:
   0.1-3.0% (w/w) of said hydrogen peroxide,
   25-1200 mg/L of said stabilizer,
   0-10 mM of one or more buffers,
   0-300 mM of an osmolality increasing agent, and
   a balance of pure water.

5. The catheter assembly according to claim 1, wherein the chelator is selected from the group consisting of diethylenetriaminepentaacetic acid (DETAPAC), deferoxamine, and diethylenetriaminepenta(methylenephosphonic acid) (DETAPMP).

6. A catheter assembly comprising:
   (i) at least one catheter element with a hydrophilic coating covering at least a part of said element;
   (ii) at least one liquid for swelling said hydrophilic coating;
   (iii) an aqueous solution of hydrogen peroxide in at least a portion of said liquid for swelling, said aqueous solution of hydrogen peroxide having a pH value of from 3.0 to 5.0 and including a stabilizer that is a chelator; and
   (iv) a packing structure having a first compartment that holds said catheter element and a second compartment that releasably holds at least said aqueous solution of hydrogen peroxide, said second compartment being a pouch closed by a rupturable closure that ruptures upon application of pressure to an exterior of said pouch to release said aqueous solution of hydrogen peroxide to said first compartment so as to swell said hydrophilic coating under sterile conditions, said aqueous solution of hydrogen peroxide being releasably contained in said second compartment so as to be separate from said first compartment, and said first compartment holds at least another portion of said liquid for swelling.

7. A catheter assembly comprising:
   (i) at least one catheter element with a hydrophilic coating covering at least a part of said element;
   (ii) at least one liquid for swelling said hydrophilic coating;
   (iii) an aqueous solution of hydrogen peroxide in at least a portion of said liquid for swelling, said aqueous solution of hydrogen peroxide having a pH value of from 3.0 to 5.0 and including a stabilizer that is a chelator; and
   (iv) a packing structure that includes a first compartment that holds said catheter element, said first compartment having an end wall with an inlet opening therein, and a second compartment that releasably holds at least said aqueous solution of hydrogen peroxide, said second compartment being (a) a rigid container having an end wall with an outlet opening therein and arranged opposite from and facing said first compartment end wall and (b) configured to be rotatable with respect to said first compartment so as to align said outlet opening with said inlet opening to release said aqueous solution of hydrogen peroxide to said first compartment so as to swell said hydrophilic coating under sterile conditions, said aqueous solution of hydrogen peroxide being releasably contained in said second compartment so as to be separate from said first compartment, and said first compartment holds at least another portion of said liquid for swelling.

* * * * *